(12) United States Patent
Cohen et al.

(10) Patent No.: US 7,796,266 B2
(45) Date of Patent: Sep. 14, 2010

(54) OPTICAL DETECTION SYSTEM USING ELECTROMAGNETIC RADIATION TO DETECT PRESENCE OR QUANTITY OF ANALYTE

(75) Inventors: David Samuel Cohen, Alpharetta, GA (US); Xuedong Song, Roswell, GA (US); Michael Knotts, Roswell, GA (US); Shawn Ray Feaster, Duluth, GA (US); Zdravko Savov Atanassov, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 515 days.

(21) Appl. No.: 11/022,287

(22) Filed: Dec. 22, 2004

(65) Prior Publication Data
US 2005/0243321 A1 Nov. 3, 2005

Related U.S. Application Data

(60) Provisional application No. 60/608,941, filed on Apr. 30, 2004.

(51) Int. Cl.
*G01N 21/00* (2006.01)
(52) U.S. Cl. .......................... 356/440; 356/39; 356/244
(58) Field of Classification Search ......... 356/244–246, 356/409, 413, 436, 440–442, 39–42, 432, 356/32–35; 435/7.4–7.95, 288.7
See application file for complete search history.

(56) References Cited

U.S. PATENT DOCUMENTS

| | | | |
|---|---|---|---|
| 3,835,247 A | 9/1974 | Soames | |
| 3,884,553 A | 5/1975 | Graser, Jr. | |
| 4,059,405 A | 11/1977 | Sodickson et al. | |
| 4,097,776 A | 6/1978 | Allinikov | |

(Continued)

FOREIGN PATENT DOCUMENTS

EP 0205698 A1 12/1986

(Continued)

OTHER PUBLICATIONS

Article—*A New Tetradentate β-Diketonate-Europium Chelate That Can Be Covalently Bound to Proteins for Time-Resolved Fluoroimmunoassay*, Jingli Yuan and Kazuko Matsumoto, Analytical Chemistry, vol. 70, No. 3, Feb. 1, 1998, pp. 596-601.

(Continued)

*Primary Examiner*—Tarifur Chowdhury
*Assistant Examiner*—Tara S Pajoohi
(74) *Attorney, Agent, or Firm*—Dority & Manning, P.A.

(57) ABSTRACT

A system that employs transmission-based detection techniques to determine the presence or concentration of an analyte within a test sample is provided. Specifically, the optical detection system contains a chromatographic-based assay device that is positioned in the electromagnetic radiation path defined between an illumination source and detector. To enhance the sensitivity and signal-to-noise ratio of the system without significantly increasing costs, the distance between the illumination source and/or detector and the assay device is minimized. The illumination source and/or detector may also be positioned directly adjacent to the assay device. In addition, the system may be selectively controlled to reduce reliance on external optical components, such as optical filters or diffusers.

20 Claims, 11 Drawing Sheets

U.S. PATENT DOCUMENTS

| | | |
|---|---|---|
| 4,168,146 A | 9/1979 | Grubb et al. |
| 4,235,601 A | 11/1980 | Deutsch et al. |
| 4,259,574 A | 3/1981 | Carr et al. |
| 4,363,874 A | 12/1982 | Greenquist |
| 4,366,241 A | 12/1982 | Tom et al. |
| 4,435,504 A | 3/1984 | Zuk et al. |
| 4,442,204 A | 4/1984 | Greenquist et al. |
| 4,480,042 A | 10/1984 | Craig et al. |
| 4,513,023 A | 4/1985 | Wary |
| 4,537,861 A | 8/1985 | Elings et al. |
| 4,560,902 A | 12/1985 | Kardon |
| 4,614,723 A | 9/1986 | Schmidt et al. |
| 4,632,559 A | 12/1986 | Brunsting |
| 4,632,807 A | 12/1986 | Marsoner |
| 4,636,626 A | 1/1987 | Hazama et al. |
| 4,647,544 A | 3/1987 | Nicoli et al. |
| 4,714,682 A | 12/1987 | Schwartz |
| 4,806,312 A | 2/1989 | Greenquist |
| 4,815,843 A | 3/1989 | Tiefenthaler et al. |
| 4,818,710 A | 4/1989 | Sutherland et al. |
| 4,843,021 A | 6/1989 | Noguchi et al. |
| 4,867,908 A | 9/1989 | Recktenwald et al. |
| 4,868,126 A | 9/1989 | Schwartz |
| 4,877,747 A | 10/1989 | Stewart |
| 4,948,975 A | 8/1990 | Erwin et al. |
| 4,992,385 A | 2/1991 | Godfrey |
| 4,999,489 A | 3/1991 | Huggins |
| RE33,581 E | 4/1991 | Nicoli |
| 5,045,474 A | 9/1991 | Becker et al. |
| 5,051,162 A | 9/1991 | Kambara et al. |
| 5,055,265 A | 10/1991 | Finlan |
| 5,075,077 A | 12/1991 | Durley, III et al. |
| 5,100,238 A | 3/1992 | Nailor et al. |
| 5,114,676 A | 5/1992 | Leiner et al. |
| 5,137,609 A | 8/1992 | Manian et al. |
| 5,166,079 A | 11/1992 | Blackwood et al. |
| 5,169,787 A | 12/1992 | Knappe et al. |
| 5,196,350 A | 3/1993 | Backman et al. |
| 5,208,535 A | 5/1993 | Nakayama et al. |
| 5,223,220 A | 6/1993 | Fan et al. |
| 5,225,935 A | 7/1993 | Watanabe et al. |
| 5,248,479 A | 9/1993 | Parsons et al. |
| 5,252,459 A | 10/1993 | Tarcha et al. |
| 5,262,299 A | 11/1993 | Evangelista et al. |
| 5,316,727 A | 5/1994 | Suzuki et al. |
| 5,321,492 A | 6/1994 | Detwiler et al. |
| 5,352,582 A | 10/1994 | Lichtenwalter et al. |
| 5,352,951 A | 10/1994 | Kardon et al. |
| 5,374,563 A | 12/1994 | Maule |
| 5,395,754 A | 3/1995 | Lambotte et al. |
| 5,418,136 A | 5/1995 | Miller et al. |
| 5,424,841 A | 6/1995 | Van Gelder et al. |
| 5,454,892 A | 10/1995 | Kardon et al. |
| 5,463,283 A | 10/1995 | Sanderson |
| 5,464,741 A | 11/1995 | Hendrix |
| 5,468,606 A | 11/1995 | Bogart et al. |
| 5,489,988 A | 2/1996 | Ackley et al. |
| 5,496,701 A | 3/1996 | Pollard-Knight |
| 5,504,013 A | 4/1996 | Senior |
| 5,508,171 A | 4/1996 | Walling et al. |
| 5,512,131 A | 4/1996 | Kumar et al. |
| 5,512,757 A | 4/1996 | Cederstrand et al. |
| 5,518,883 A | 5/1996 | Soini |
| 5,534,132 A | 7/1996 | Vreeke et al. |
| 5,534,386 A | 7/1996 | Petersen et al. |
| 5,554,531 A | 9/1996 | Zweig |
| 5,573,909 A | 11/1996 | Singer et al. |
| 5,585,279 A | 12/1996 | Davidson |
| 5,589,401 A | 12/1996 | Hansen et al. |
| 5,591,581 A | 1/1997 | Massey et al. |
| 5,599,668 A | 2/1997 | Stimpson et al. |
| 5,604,351 A | 2/1997 | Bisconte |
| 5,618,732 A | 4/1997 | Pease et al. |
| 5,622,872 A | 4/1997 | Ribi |
| 5,624,537 A | 4/1997 | Turner et al. |
| 5,637,509 A | 6/1997 | Hemmilä et al. |
| 5,670,381 A | 9/1997 | Jou et al. |
| 5,674,698 A | 10/1997 | Zarling et al. |
| 5,686,797 A | 11/1997 | Sanderson |
| 5,698,406 A | 12/1997 | Cathey et al. |
| 5,731,147 A | 3/1998 | Bard et al. |
| 5,738,825 A | 4/1998 | Rudigier et al. |
| 5,764,355 A * | 6/1998 | Gagnon et al. ............. 356/244 |
| 5,770,389 A * | 6/1998 | Ching et al. ............... 435/7.92 |
| 5,814,565 A | 9/1998 | Reichert et al. |
| 5,827,748 A | 10/1998 | Golden |
| 5,848,977 A | 12/1998 | Zakim et al. |
| 5,892,577 A | 4/1999 | Gordon |
| 5,910,940 A | 6/1999 | Guerra |
| 5,922,537 A | 7/1999 | Ewart et al. |
| 5,922,550 A | 7/1999 | Everhart et al. |
| 5,943,129 A | 8/1999 | Hoyt et al. |
| 5,968,839 A | 10/1999 | Blatt et al. |
| 5,976,892 A | 11/1999 | Bisconte |
| 6,004,530 A | 12/1999 | Sagner et al. |
| 6,004,686 A | 12/1999 | Rasmussen et al. |
| 6,020,047 A | 2/2000 | Everhart |
| 6,030,840 A | 2/2000 | Mullinax et al. |
| 6,048,623 A | 4/2000 | Everhart et al. |
| 6,057,165 A | 5/2000 | Mansour |
| 6,060,256 A | 5/2000 | Everhart et al. |
| 6,084,683 A | 7/2000 | Bruno et al. |
| 6,136,268 A | 10/2000 | Ala-Kleme et al. |
| 6,136,610 A * | 10/2000 | Polito et al. ................. 436/514 |
| 6,136,611 A | 10/2000 | Saaski et al. |
| 6,159,703 A | 12/2000 | Menton et al. |
| 6,165,798 A | 12/2000 | Brooks |
| 6,166,804 A * | 12/2000 | Potyrailo et al. ............ 356/318 |
| 6,180,288 B1 | 1/2001 | Everhart et al. |
| 6,187,269 B1 | 2/2001 | Lancesseur et al. |
| 6,194,220 B1 | 2/2001 | Malick et al. |
| 6,197,503 B1 | 3/2001 | Vo-Dinh et al. |
| 6,200,820 B1 | 3/2001 | Hansen et al. |
| 6,207,369 B1 | 3/2001 | Wohlstadter et al. |
| 6,221,579 B1 | 4/2001 | Everhart et al. |
| 6,235,241 B1 | 5/2001 | Catt et al. |
| 6,241,863 B1 | 6/2001 | Monbouquette |
| 6,242,268 B1 | 6/2001 | Wieder et al. |
| 6,261,779 B1 | 7/2001 | Barbera-Guillem et al. |
| 6,270,637 B1 | 8/2001 | Crismore et al. |
| 6,274,384 B1 | 8/2001 | Starzl et al. |
| 6,281,006 B1 | 8/2001 | Heller et al. |
| 6,287,783 B1 | 9/2001 | Maynard et al. |
| 6,287,871 B1 | 9/2001 | Herron et al. |
| 6,294,392 B1 | 9/2001 | Kuhr et al. |
| 6,331,438 B1 | 12/2001 | Aylott et al. |
| 6,335,203 B1 | 1/2002 | Patel et al. |
| 6,362,011 B1 | 3/2002 | Massey et al. |
| 6,372,511 B1 | 4/2002 | Silver et al. |
| 6,396,053 B1 | 5/2002 | Yokoi |
| 6,399,295 B1 | 6/2002 | Kaylor et al. |
| 6,399,398 B1 | 6/2002 | Cunningham et al. |
| 6,411,439 B2 | 6/2002 | Nishikawa |
| 6,416,642 B1 | 7/2002 | Alajoki et al. |
| 6,426,213 B1 * | 7/2002 | Eisenson ................. 435/288.7 |
| 6,432,516 B1 | 8/2002 | Terasaki et al. |
| 6,436,651 B1 | 8/2002 | Everhart et al. |
| 6,436,722 B1 | 8/2002 | Clark et al. |
| 6,444,423 B1 | 9/2002 | Meade et al. |
| 6,448,091 B1 | 9/2002 | Massey et al. |
| 6,461,496 B1 | 10/2002 | Feldman et al. |
| 6,468,741 B1 | 10/2002 | Massey et al. |
| 6,479,930 B1 | 11/2002 | Tanabe et al. |
| 6,481,453 B1 | 11/2002 | O'Connor et al. |

| | | | |
|---|---|---|---|
| 6,483,582 B2 | 11/2002 | Modlin | |
| 6,485,962 B1 | 11/2002 | Tabacco et al. | |
| 6,498,690 B2 | 12/2002 | Ramm et al. | |
| 6,509,085 B1 | 1/2003 | Kennedy | |
| 6,519,355 B2 | 2/2003 | Nelson | |
| 6,556,299 B1 | 4/2003 | Rushbrooke et al. | |
| 6,566,508 B2 | 5/2003 | Bentsen et al. | |
| 6,573,040 B2 | 6/2003 | Everhart et al. | |
| 6,579,673 B2 | 6/2003 | McGrath et al. | |
| 6,580,507 B2* | 6/2003 | Fry et al. | 356/436 |
| 6,582,930 B1 | 6/2003 | Ponomarev et al. | |
| 6,585,939 B1 | 7/2003 | Dapprich | |
| 6,602,618 B2 | 8/2003 | Watanabe et al. | |
| 6,607,922 B2 | 8/2003 | LaBorde | |
| 6,613,583 B1 | 9/2003 | Richter et al. | |
| 6,642,652 B2 | 11/2003 | Collins, III et al. | |
| 6,709,695 B2 | 3/2004 | Takeishi et al. | |
| 6,723,192 B2 | 4/2004 | Nagano et al. | |
| 6,734,469 B2 | 5/2004 | Yano et al. | |
| 6,759,121 B2 | 7/2004 | Alahapperuma et al. | |
| 6,759,235 B2 | 7/2004 | Empedocles et al. | |
| 6,861,264 B2 | 3/2005 | Mabile et al. | |
| 6,867,851 B2 | 3/2005 | Blumenfeld et al. | |
| 6,873,410 B2 | 3/2005 | Tanaami et al. | |
| 7,186,566 B2 | 3/2007 | Qian | |
| 2002/0004246 A1* | 1/2002 | Daniels et al. | 436/514 |
| 2002/0083858 A1 | 7/2002 | MacDiarmid et al. | |
| 2002/0094548 A1 | 7/2002 | Feistel | |
| 2002/0173044 A1* | 11/2002 | Pachl et al. | 436/67 |
| 2003/0107740 A1 | 6/2003 | Kaylor et al. | |
| 2003/0118480 A1 | 6/2003 | Kaylor et al. | |
| 2003/0119202 A1 | 6/2003 | Kaylor et al. | |
| 2003/0124739 A1 | 7/2003 | Song et al. | |
| 2003/0143580 A1 | 7/2003 | Straus | |
| 2003/0164024 A1 | 9/2003 | Mitsubayashi et al. | |
| 2003/0180807 A1 | 9/2003 | Hess et al. | |
| 2003/0193289 A1 | 10/2003 | Shirakawa et al. | |
| 2003/0207253 A1 | 11/2003 | Kaylor et al. | |
| 2003/0235924 A1* | 12/2003 | Adams et al. | 436/172 |
| 2004/0002110 A1 | 1/2004 | Boga et al. | |
| 2004/0043502 A1 | 3/2004 | Song et al. | |
| 2004/0043507 A1 | 3/2004 | Song et al. | |
| 2004/0043511 A1 | 3/2004 | Song et al. | |
| 2004/0043512 A1 | 3/2004 | Song et al. | |
| 2004/0063146 A1 | 4/2004 | Sayre et al. | |
| 2004/0070195 A1 | 4/2004 | Nelson et al. | |
| 2004/0119400 A1 | 6/2004 | Takahashi et al. | |
| 2005/0244952 A1* | 11/2005 | Cohen | 435/287.2 |
| 2005/0244953 A1* | 11/2005 | Cohen | 435/287.2 |
| 2006/0019265 A1* | 1/2006 | Song et al. | 435/6 |
| 2006/0258020 A1 | 11/2006 | Kao et al. | |
| 2007/0048815 A1 | 3/2007 | Song | |
| 2007/0121113 A1* | 5/2007 | Cohen et al. | 356/432 |

FOREIGN PATENT DOCUMENTS

| | | |
|---|---|---|
| EP | 0283285 A2 | 9/1988 |
| EP | 0283285 A3 | 9/1988 |
| EP | 0791821 A1 | 8/1997 |
| EP | 0811842 A1 | 12/1997 |
| EP | 0898169 B1 | 2/1999 |
| WO | WO 9105999 A2 | 5/1991 |
| WO | WO 9301308 A1 | 1/1993 |
| WO | WO 9322453 A1 | 11/1993 |
| WO | WO 9413835 A1 | 6/1994 |
| WO | WO 9415193 A1 | 7/1994 |
| WO | WO 9513531 | 5/1995 |
| WO | WO 9609532 A1 | 3/1996 |
| WO | WO 9612962 A1 | 5/1996 |
| WO | WO 9703347 A1 | 1/1997 |
| WO | WO 9721090 A1 | 6/1997 |
| WO | WO 9915858 A1 | 4/1999 |
| WO | WO 0050891 A1 | 8/2000 |
| WO | WO 03001889 A2 | 1/2003 |
| WO | WO 03001889 A3 | 1/2003 |
| WO | WO 03008971 A2 | 1/2003 |
| WO | WO 03008971 A3 | 1/2003 |
| WO | WO 03104384 A1 | 12/2003 |
| WO | WO 2004044560 A1 | 5/2004 |
| WO | WO 2004048881 A2 | 6/2004 |
| WO | WO 2004048881 A3 | 11/2004 |
| WO | WO 2005/111577 A1 | 11/2005 |
| WO | WO 2005/111579 A1 | 11/2005 |

OTHER PUBLICATIONS

Article—*Evaluation of a Time-Resolved Fluorescence Microscope Using a Phosphorescent Pt-Porphine Model System*, E. J. Hennink, R. de Haas, N. P. Verwoerd, and H. J. Tanke, Cytometry, vol. 24, 1996, pp. 312-320.

Article—*How to Build a Spectrofluorometer*, Spex Fluorolog 3, Horiba Group, pp. 1-14.

Article—*Indium tin oxide contacts to gallium nitride optoelectronic devices*, T. Margalith, O. Buchinsky, D. A. Cohen, A. C. Abare, M. Hansen, S. P. DenBaars, and L. A. Coldren, Applied Physics Letters, vol. 74, No. 26, Jun. 28, 1999, pp. 3930-3932.

Article—*Longwave luminescent porphyrin probes*, Dmitry B. Papkovsky, Gelii P. Ponomarev, and Otto S. Wolfbeis, Spectrochimica Acta Part A 52, 1996, pp. 1629-1638.

Article—*One-step all-in-one dry reagent immunoassays with fluorescent europium chelate label and time-resolved fluorometry*, Timo Lövgren, Liisa Meriö, Katja Mitrunen, Maija-Lusa Mäkinen, Minna Mäkelä, Kaj Blomberg, Tom Palenius, and Kim Pettersson, Clinical Chemistry, vol. 42, No. 8, 1996, pp. 1196-1201.

Article—*Optical Biosensor Assay (OBA™)*, Y. G. Tsay, C. I. Lin, J. Lee, E. K. Gustafson, R. Appelqvist, P. Magginetti, R. Norton, N. Teng, and D. Charlton, Clinical Chemistry, vol. 37, No. 9, 1991, pp. 1502-1505.

Article—*Polymer Based Lanthanide Luminescent Sensors for the Detection of Nerve Agents*, Amanda L. Jenkins, O. Manuel Uy, and George M. Murray, Analytical Communications, vol. 34, Aug. 1997, pp. 221-224.

EL Lamps articles from DuPont Microcircuit Materials, 2 pages, www.dupont.com.

Product Description of Test Strip Reader TSR 3000 from BioDot, Inc., 2 pages.

Product Information from BKL, Inc. on Screen Printed Electroluminescent (EL) Lamps, 2 pages, www.eluminate.com.

Technical Bulletin from Tobias Associates, Inc. entitled *Reflection Densitometry*, 10 pages, www.ourworld.compuserve.com.

Article—*DNA Biochip Using a Phototransistor Integrated Circuit*, Vo-Dinh et al., Analytical Chemistry, vol. 71, No. 2, Jan. 15, 1999, pp. 358-363.

Search Report and Written Opinion for PCT/US2005/014121, Sep. 23, 2005.

Search Report and Written Opinion for PCT/US2005/011053, Sep. 28, 2005.

Search Report and Written Opinion for PCT/US2005/014123, Sep. 2, 2005.

Search Report and Written Opinion for PCT/US2005/014124, Sep. 13, 2005.

David S. Cohen, U.S. Appl. No. 11/022,286, filed Dec. 22, 2004, Techniques For Controlling The Optical Properties Of Assay Devices.

David S. Cohen, U.S. Appl. No. 11/022,285, filed Dec. 22, 2004, Electroluminscent Illumination Source For Optical Systems.

Song, et al. U.S. Appl. No. 11/020,647, filed Dec. 22, 2004, Transmission-Based Luminescent Detection Systems.

Search Report and Written Opinion for PCT/IB2007/052811, Jan. 24, 2008.

* cited by examiner

OPTICAL DETECTION SYSTEM USING ELECTROMAGNETIC RADIATION TO DETECT PRESENCE OR QUANTITY OF ANALYTE

RELATED APPLICATIONS

The present application claims priority to a provisional application having Ser. No. 60/608,941, which was filed on Apr. 30, 2004.

BACKGROUND OF THE INVENTION

Optical detection systems are often utilized to qualitatively, quantitatively, or semi-quantitatively determine the presence or concentration of an analyte within a test sample. Unfortunately, conventional optical detection systems generally suffer from at least one of two major problems. One problem is that the optical detection system, although sensitive and accurate, is too expensive and complex for use by ordinary consumers, such as non-technical personnel at doctor's offices, clinics, home, rest homes, etc. To reduce cost and complexity, other optical detection systems have thus been developed. However, such systems typically achieve a reduction in cost and complexity through a concurrent loss in sensitivity. Although such a loss in sensitivity is not necessarily critical in all applications, it becomes increasingly problematic when the system is used in conjunction with membrane-based assay devices. Specifically, analyte concentration is diluted in such devices by fluid flowing through the membrane. Due to such a low analyte concentration, the level of background interference (i.e., "noise") may simply be too great relative to the detection signal to achieve an accurate result.

As such, a need currently exists for a more "balanced" optical detection system for assay devices that is easy to use, inexpensive, and possesses an increased signal-to-noise ratio.

SUMMARY OF THE INVENTION

In accordance with one embodiment of the present invention, an optical detection system is disclosed for detecting the presence or quantity of an analyte residing in a test sample. The system comprises an assay device that includes a chromatographic medium in communication with detection probes, the detection probes being capable of producing a detection signal. The system also includes an illumination source capable of providing electromagnetic radiation that causes the detection probes to produce the detection signal, and a detector capable of registering the detection signal produced by the detection probes. The illumination source and detector are positioned on opposing sides of the assay device so that the chromatographic medium is positioned in the electromagnetic radiation path defined between the illumination source and the detector. The chromatographic medium is transmissive to the electromagnetic radiation and the detection signal. In addition, the illumination source, detector, or both, are positioned less than about 5 millimeters from the assay device.

In accordance with another embodiment of the present invention, an optical detection system is disclosed for detecting the presence or quantity of an analyte residing in a test sample. The system comprises an assay device that includes a porous membrane carried by a support. The porous membrane is in communication with detection probes that are capable of producing a detection signal. The system also includes an illumination source capable of providing electromagnetic radiation that causes the detection probes to produce the detection signal, and a detector capable of registering the detection signal produced by the detection probes. The illumination source and detector are positioned on opposing sides of the assay device so that the porous membrane is positioned in the electromagnetic radiation path defined between the illumination source and the detector. The porous membrane is transmissive to the electromagnetic radiation and the detection signal. In addition, the illumination source, detector, or both, are positioned less than about 5 millimeters from the assay device.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figure in which:

FIG. 3 schematically illustrates various embodiments of the optical detection system of the present invention, in which

FIG. 5 is a perspective view of one embodiment of a sample holder that may be used in the present invention, in which

Figure 1:
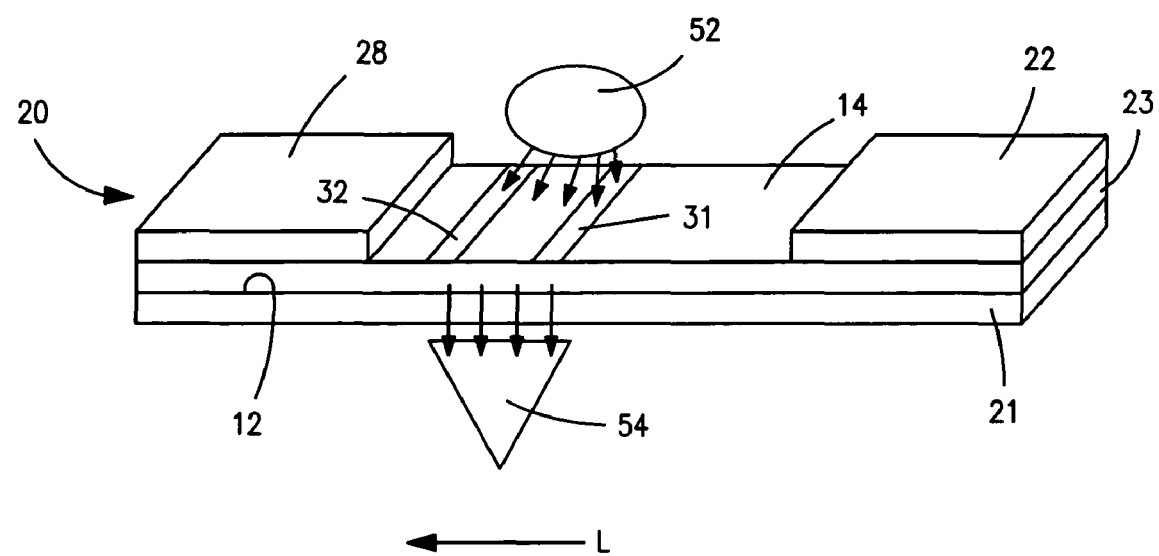
FIG. 1 is a perspective view of one embodiment of an optical detection system of the present invention.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "analyte" generally refers to a substance to be detected. For instance, analytes may include antigenic substances, haptens, antibodies, and combinations thereof. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), drug intermediaries or byproducts, bacteria, virus particles and metabolites of or antibodies to any of the above substances. Specific examples of some analytes include ferritin; creatinine kinase MB (CK-MB); digoxin; phenyloin; phenobarbitol; carbamazepine; vancomycin; gentamycin; theophylline; valproic acid; quinidine; luteinizing hormone (LH); follicle stimulating hormone (FSH); estradiol, progesterone; C-reactive protein; lipocalins; IgE antibodies; cytokines; vitamin B2 microglobulin; glycated hemoglobin (Gly. Hb); cortisol; digitoxin; N-acetylprocainamide (NAPA); procainamide; antibodies to rubella, such as rubella-IgG and rubella IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg); antibodies to hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis B e antigen (HBeAg); antibodies to hepatitis B e antigen (Anti-HBe); influenza virus; thyroid stimulating hormone (TSH); thyroxine (T4); total triiodothyronine (Total T3); free triiodothyronine (Free T3); carcinoembryoic antigen (CEA); lipoproteins, cholesterol, and triglycerides; and alpha fetoprotein (AFP). Drugs of abuse and controlled substances include, but are not intended to be limited to, amphetamine; methamphetamine; barbiturates, such as amobarbital, secobarbital, pentobarbital, phenobarbital, and barbital; benzodiazepines, such as librium and valium; cannabinoids, such as hashish and marijuana; cocaine; fentanyl; LSD; methaqualone; opiates, such as heroin, morphine, codeine, hydromorphone, hydrocodone, methadone, oxycodone, oxymorphone and opium; phencyclidine; and propoxyhene. Other potential analytes may be described in U.S. Pat. No. 6,436,651 to Everhart, et al. and U.S. Pat. No. 4,366,241 to Tom et al.

As used herein, the term "test sample" generally refers to a biological material suspected of containing the analyte. The test sample may be derived from any biological source, such as a physiological fluid, including, blood, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid, semen, and so forth. Besides physiological fluids, other liquid samples may be used such as water, food products, and so forth, for the performance of environmental or food production assays. In addition, a solid material suspected of containing the analyte may be used as the test sample. The test sample may be used directly as obtained from the biological source or following a pretreatment to modify the character of the sample. For example, such pretreatment may include preparing plasma from blood, diluting viscous fluids, and so forth. Methods of pretreatment may also involve filtration, precipitation, dilution, distillation, mixing, concentration, inactivation of interfering components, the addition of reagents, lysing, etc. Moreover, it may also be beneficial to modify a solid test sample to form a liquid medium or to release the analyte.

DETAILED DESCRIPTION

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

In general, the present invention is directed to a system that employs transmission-based detection techniques to determine the presence or concentration of an analyte within a test sample. Specifically, the optical detection system contains a chromatographic-based assay device that is positioned in the electromagnetic radiation path defined between an illumination source and detector. To enhance the sensitivity and signal-to-noise ratio of the system without significantly increasing costs, the distance between the illumination source and/or detector and the assay device is minimized. The illumination source and/or detector may also be positioned directly adjacent to the assay device. In addition, the system may be selectively controlled to reduce reliance on external optical components, such as optical filters or diffusers. For example, an illumination source that emits diffuse light, such as an electroluminescent (EL) device, may be utilized to reduce reliance on diffusers typically required for point light sources, such as LEDs. Thus, unlike many conventional systems, the optical detection system of the present invention is portable, simple to use, inexpensive, and possesses an enhanced sensitivity and signal-to-noise ratio.

I. Assay Device

Generally speaking, the assay device employed in the present invention is configured to perform a heterogeneous immunoassay. A heterogeneous assay is an assay in which uncomplexed labeled species are separated from complexed labeled species. Separation may be carried out by physical separation, e.g., by transferring one of the species to another reaction vessel, filtration, centrifugation, chromatography, solid phase capture, magnetic separation, and so forth, and may include one or more washing steps. The separation may also be nonphysical in that no transfer of one or both of the species is conducted, but the species are separated from one another in situ. In one particular embodiment, for example, a heterogeneous immunoassay is performed. Such immunoassays utilize mechanisms of the immune systems, wherein antibodies are produced in response to the presence of antigens that are pathogenic or foreign to the organisms. These antibodies and antigens, i.e., immunoreactants, are capable of binding with one another, thereby causing a highly specific reaction mechanism that may be used to determine the presence or concentration of that particular antigen in a fluid test sample.

Referring to FIG. 1, for example, one embodiment of a chromatographic-based assay device 20 that is configured to perform a heterogeneous immunoassay will now be described in more detail. As shown, the assay device 20 contains a chromatographic medium 23 having a first surface 12 and an opposing second surface 14. The first surface 12 of the medium 23 is positioned adjacent to a support 21. The chromatographic medium 23 is generally made from a material through which the test sample is capable of passing, such as a fluidic channel, porous membrane, etc. Likewise, the medium 23 is also made from a material through which electromagnetic radiation may transmit, such as an optically diffuse (e.g., translucent) or transparent material. In one particular embodiment, for example, the chromatographic medium 23 is made from an optically diffuse porous membrane formed from materials such as, but not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth. In one particular embodiment, the chromatographic medium 23 is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The size and shape of the chromatographic medium 23 may generally vary as is readily recognized by those skilled in the art. For instance, a porous membrane strip may have a length of from about 10 to about 100 millimeters, in some embodiments from about 20 to about 80 millimeters, and in some embodiments, from about 40 to about 60 millimeters. The width of the membrane strip may also range from about 0.5 to about 20 millimeters, in some embodiments from about 1 to about 15 millimeters, and in some embodiments, from about 2 to about 10 millimeters. Likewise, the thickness of the membrane strip is generally small enough to allow transmission-based detection. For example, the membrane strip may have a thickness less than about 500 micrometers, in some embodiments less than about 250 micrometers, and in some embodiments, less than about 150 micrometers.

As stated above, the support 21 carries the chromatographic medium 23. For example, the support 21 may be positioned directly adjacent to the chromatographic medium 23 as shown in FIG. 1, or one or more intervening layers may be positioned between the chromatographic medium 23 and the support 21. Regardless, the support 21 may generally be formed from any material able to carry the chromatographic medium 23. Generally, the support 21 is formed from a material that is transmissive to light, such as transparent or optically diffuse (e.g., translucent) materials. Also, it is generally desired that the support 21 is liquid-impermeable so that fluid flowing through the medium 23 does not leak through the support 21. Examples of suitable materials for the support include, but are not limited to, glass; polymeric materials, such as polystyrene, polypropylene, polyester (e.g., Mylar® film), polybutadiene, polyvinylchloride, polyamide, polycarbonate, epoxides, methacrylates, and polymelamine; and so forth. To provide a sufficient structural backing for the chromatographic medium 23, the support 21 is generally selected to have a certain minimum thickness. Likewise, the thickness of the support 21 is typically not so large as to adversely affect its optical properties. Thus, for example, the support 21 may have a thickness that ranges from about 100 to about 5,000 micrometers, in some embodiments from about 150 to about 2,000 micrometers, and in some embodiments, from about 250 to about 1,000 micrometers. For instance, one suitable membrane strip having a thickness of about 125 micrometers may be obtained from Millipore Corp. of Bedford, Mass. under the name "SHF180UB25."

As is well known the art, the chromatographic medium 23 may be cast onto the support 21, wherein the resulting laminate may be die-cut to the desired size and shape. Alternatively, the chromatographic medium 23 may simply be laminated to the support 21 with, for example, an adhesive. In some embodiments, a nitrocellulose or nylon porous membrane is adhered to a Mylar® film. An adhesive is used to bind the porous membrane to the Mylar® film, such as a pressure-sensitive adhesive. Laminate structures of this type are believed to be commercially available from Millipore Corp. of Bedford, Mass. Still other examples of suitable laminate assay device structures are described in U.S. Pat. No. 5,075,077 to Durley, III, et al., which is incorporated herein in its entirety by reference thereto for all purposes.

The selection of an adhesive for laminating the support 21, the chromatographic medium 23, and/or any other layer of the device may depend on a variety of factors, including the desired optical properties of the detection system and the materials used to form the assay device. For example, in some embodiments, the selected adhesive is optically transparent and compatible with the chromatographic medium 23 and support 21. Optical transparency may minimize any adverse affect that the adhesive might otherwise have on the optical detection system. Suitable optically transparent adhesives may be formed, for instance, from acrylate or (meth)acrylate polymers, such as polymers of (meth)acrylate esters, acrylic or (meth)acrylic acid monomers, and so forth. Exemplary (meth)acrylate ester monomers include monofunctional acrylate or methacrylate esters of non-tertiary alkyl alcohols, such as methyl acrylate, ethyl acrylate, propyl acrylate, n-butyl acrylate, isobutyl acrylate, 2-methylbutyl acrylate, 2-ethylhexyl acrylate, 2-ethylhexyl methacrylate, n-octyl acrylate, n-octyl methacrylate, isooctyl acrylate, isooctyl methacrylate, isononyl acrylate, isodecyl acrylate, isobornyl acrylate, isobornyl methacrylate, vinyl acetate, and mixtures thereof. Exemplary (meth)acrylic acid monomers include acrylic acid, methacrylic acid, beta-carboxyethyl acrylate, itaconic acid, crotonic acid, fumaric acid, and so forth. Several examples of such optically transparent adhesives are described in U.S. Pat. No. 6,759,121 to Alahapperuma, et al., which is incorporated herein in its entirety by reference thereto for all purposes. Further, suitable transparent adhesives may also be obtained from Adhesives Research, Inc. of Glen Rock, Pa. under the name ARclear® 8154, which is an unsupported optically clear acrylic pressure-sensitive adhesive. Other suitable transparent adhesives may be obtained from 3M Corp. of St. Paul, Minn. under the names "9843" or "8146." In addition, the manner in which the adhesive is applied may also enhance the optical properties of the assay device. For instance, the adhesive may enhance certain optical properties of the support (e.g., diffusiveness). Thus, in one particular embodiment, such an adhesive may be applied in a pattern that corresponds to the areas in which enhanced optical properties are desired.

Referring again to FIG. 1, an absorbent pad 28 is provided on the second surface 14 that generally receives fluid after it migrates through the entire chromatographic medium 23. As is well known in the art, the absorbent pad 28 may also assist in promoting capillary action and fluid flow through the chromatographic medium 23. To initiate the detection of an analyte within the test sample, a user may directly apply the test sample to a portion of the chromatographic medium 23 through which it may then travel in the direction illustrated by arrow "L" in FIG. 1. Alternatively, the test sample may first be applied to a sample pad (not shown) that is in fluid communication with the chromatographic medium 23. Some suitable materials that may be used to form the absorbent pad 28 and/or sample pad include, but are not limited to, nitrocellulose, cellulose, porous polyethylene pads, and glass fiber filter paper. If desired, the sample pad may also contain one or more assay pretreatment reagents, either diffusively or non-diffusively attached thereto.

In the illustrated embodiment, the test sample travels from the sample pad (not shown) to a conjugate pad 22 that is placed in communication with one end of the sample pad. The conjugate pad 22 is formed from a material through which a fluid is capable of passing. For example, in one embodiment, the conjugate pad 22 is formed from glass fibers. Although only one conjugate pad 22 is shown, it should be understood that other conjugate pads may also be used in the present invention.

To facilitate accurate detection of the presence or absence of an analyte within the test sample, a predetermined amount of detection probes may be applied at various locations of the assay device 20. Such detection probes contain a substance that directly or indirectly produces an optically detectable signal, such as molecules, polymers, dendrimers, and so forth. Suitable detectable substances may include, for instance, luminescent compounds (e.g., fluorescent, phosphorescent, etc.); radioactive compounds; visual (i.e., non-fluorescent) compounds (e.g., colored dye or metallic substance, e.g., gold); liposomes or other vesicles containing signal-producing substances; enzymes and/or substrates, and so forth. Other suitable detectable substances may be described in U.S. Pat. Nos. 5,670,381 to Jou, et al. and 5,252,459 to Tarcha, et al., which are incorporated herein in their entirety by reference thereto for all purposes. If the detectable substance is colored, the ideal electromagnetic radiation is light of a complementary wavelength. For instance, blue detection probes strongly absorb red light.

In some embodiments, the detectable substance may be a luminescent compound that produces an optically detectable signal. For example, suitable fluorescent molecules may include, but not limited to, fluorescein, europium chelates, phycobiliprotein, rhodamine, and their derivatives and analogs. Other suitable fluorescent compounds are semiconductor nanocrystals commonly referred to as "quantum dots." For example, such nanocrystals may contain a core of the formula CdX, wherein X is Se, Te, S, and so forth. The nanocrystals may also be passivated with an overlying shell of the formula YZ, wherein Y is Cd or Zn, and Z is S or Se. Other examples of suitable semiconductor nanocrystals may also be described in U.S. Pat. No. 6,261,779 to Barbera-Guillem, et al. and U.S. Pat. No. 6,585,939 to Dapprich, which are incorporated herein in their entirety by reference thereto for all purposes.

Further, suitable phosphorescent compounds may include metal complexes of one or more metals, such as ruthenium, osmium, rhenium, iridium, rhodium, platinum, indium, palladium, molybdenum, technetium, copper, iron, chromium, tungsten, zinc, and so forth. Especially preferred are ruthenium, rhenium, osmium, platinum, and palladium. The metal complex may contain one or more ligands that facilitate the solubility of the complex in an aqueous or nonaqueous environment. For example, some suitable examples of ligands include, but are not limited to, pyridine; pyrazine; isonicotinamide; imidazole; bipyridine; terpyridine; phenanthroline; dipyridophenazine; porphyrin, porphine, and derivatives thereof. Such ligands may be, for instance, substituted with alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, sulfur-containing groups, phosphorus containing groups, and the carboxylate ester of N-hydroxy-succinimide.

Porphyrins and porphine metal complexes possess pyrrole groups coupled together with methylene bridges to form cyclic structures with metal chelating inner cavities. Many of these molecules exhibit strong phosphorescence properties at room temperature in suitable solvents (e.g., water) and an oxygen-free environment. Some suitable porphyrin complexes that are capable of exhibiting phosphorescent properties include, but are not limited to, platinum (II) coproporphyrin-I and II, palladium (II) coproporphyrin, ruthenium coproporphyrin, zinc(II)-coproporphyrin-I, derivatives thereof, and so forth. Similarly, some suitable porphine complexes that are capable of exhibiting phosphorescent properties include, but not limited to, platinum(II) tetra-meso-fluorophenylporphine and palladium(II) tetra-meso-fluorophenylporphine. Still other suitable porphyrin and/or porphine complexes are described in U.S. Pat. No. 4,614,723 to Schmidt, et al.; U.S. Pat. No. 5,464,741 to Hendrix; U.S. Pat. No. 5,518,883 to Soini; U.S. Pat. No. 5,922,537 to Ewart, et al.; U.S. Pat. No. 6,004,530 to Sagner, et al.; and U.S. Pat. No. 6,582,930 to Ponomarev, et al., which are incorporated herein in their entirety by reference thereto for all purposes.

Bipyridine metal complexes may also be utilized as phosphorescent compounds. Some examples of suitable bipyridine complexes include, but are note limited to, bis[(4,4'-carbomethoxy)-2,2'-bipyridine]2-[3-(4-methyl-2,2'-bipyridine-4-yl)propyl]-1,3-dioxolane ruthenium (II); bis(2, 2'bipyridine)[4-(butan-1-al)-4'-methyl-2,2'-bi-pyridine] ruthenium (II); bis(2,2'-bipyridine)[4-(4'-methyl-2,2'-bipyridine-4'-yl)-butyric acid]ruthenium (II); tris(2, 2'bipyridine)ruthenium (II); (2,2'-bipyridine) [bis-bis(1,2-diphenylphosphino)ethylene]2-[3-(4-methyl-2,2'-bipyridine-4'-yl)propyl]-1,3-dioxolane osmium (II); bis(2,2'-bipyridine)[4-(4'-methyl-2,2'-bipyridine)-butylamine] ruthenium (II); bis(2,2'-bipyridine)[1-bromo-4(4'-methyl-2, 2'-bipyridine-4-yl)butane]ruthenium (II); bis(2,2'-bipyridine)maleimidohexanoic acid, 4-methyl-2,2'-bipyridine-4'-butylamide ruthenium (II), and so forth. Still other suitable metal complexes that may exhibit phosphorescent properties may be described in U.S. Pat. No. 6,613,583 to Richter, et al.; U.S. Pat. No. 6,468,741 to Massey, et al.; U.S. Pat. No. 6,444,423 to Meade, et al.; U.S. Pat. No. 6,362,011 to Massey, et al.; U.S. Pat. No. 5,731,147 to Bard, et al.; and U.S. Pat. No. 5,591,581 to Massey, et al., which are incorporated herein in their entirety by reference thereto for all purposes.

In some cases, "time-resolved" luminescent detection techniques may be utilized in some embodiments of the present invention. Time-resolved detection involves exciting a luminescent probe with one or more short pulses of light, then typically waiting a certain time after excitation before measuring the remaining luminescent signal, such as from about 1 to about 200 microseconds, and particularly from about 10 to about 50 microseconds. In this manner, any short-lived phosphorescent or fluorescent background signals and scattered excitation radiation are eliminated. This ability to eliminate much of the background signals may result in sensitivities that are 2 to 4 orders greater than conventional fluorescence or phosphorescence. Thus, time-resolved detection is designed to reduce background signals from the illumination source or from scattering processes (resulting from scattering of the excitation radiation) by taking advantage of the characteristics of certain luminescent materials.

To function effectively, time-resolved techniques generally require a relatively long emission lifetime for the luminescent compounds. This is desired so that the compound emits its signal well after any short-lived background signals dissipate. Furthermore, a long luminescence lifetime makes it possible to use low-cost circuitry for time-gated measurements. For example, the detectable compounds may have a luminescence lifetime of greater than about 1 microsecond, in some embodiments greater than about 10 microseconds, in some embodiments greater than about 50 microseconds, and in some embodiments, from about 100 microseconds to about 1000 microseconds. In addition, the compound may also have a relatively large "Stokes shift." The term "Stokes shift" is generally defined as the displacement of spectral lines or bands of luminescent radiation to a longer emission wavelength than the excitation lines or bands. A relatively large Stokes shift allows the excitation wavelength of a luminescent compound to remain far apart from its emission wavelengths and is desirable because a large difference between excitation and emission wavelengths makes it easier to eliminate the reflected excitation radiation from the emitted signal. Further, a large Stokes shift also minimizes interference from luminescent molecules in the sample and/or light scattering due to proteins or colloids, which are present with some body fluids (e.g., blood). In addition, a large Stokes shift also minimizes the requirement for expensive, high-precision filters to eliminate background interference. For example, in some embodiments, the luminescent compounds have a Stokes shift of greater than about 50 nanometers, in some embodiments greater than about 100 nanometers, and in some embodiments, from about 100 to about 350 nanometers.

For example, one suitable type of fluorescent compound for use in time-resolved detection techniques includes lanthanide chelates of samarium (Sm (III)), dysprosium (Dy (III)), europium (Eu (III)), and terbium (Tb (III)). Such chelates may exhibit strongly red-shifted, narrow-band, long-lived emission after excitation of the chelate at substantially shorter wavelengths. Typically, the chelate possesses a strong ultraviolet excitation band due to a chromophore located close to the lanthanide in the molecule. Subsequent to excitation by the chromophore, the excitation energy may be transferred from the excited chromophore to the lanthanide. This is followed by a fluorescence emission characteristic of the lanthanide. Europium chelates, for instance, have exceptionally large Stokes shifts of about 250 to about 350 nanometers, as compared to only about 28 nanometers for fluorescein. Also, the fluorescence of europium chelates is long-lived, with lifetimes of about 100 to about 1000 microseconds, as compared to about 1 to about 100 nanoseconds for other fluorescent labels. In addition, these chelates have a narrow emission spectra, typically having bandwidths less than about 10 nanometers at about 50% emission. One suitable europium chelate is N-(p-isothiocyanatobenzyl)-diethylene triamine tetraacetic acid-$Eu^{+3}$.

In addition, lanthanide chelates that are inert, stable, and intrinsically fluorescent in aqueous solutions or suspensions may also be used in the present invention to negate the need for micelle-forming reagents, which are often used to protect chelates having limited solubility and quenching problems in aqueous solutions or suspensions. One example of such a chelate is 4-[2-(4-isothiocyanatophenyl)ethynyl]-2,6-bis([N, N-bis(carboxymethyl)amino]methyl)-pyridine [Ref: Lovgren, T., et al.; Clin. Chem. 42, 1196-1201 (1996)]. Several lanthanide chelates also show exceptionally high signal-to-noise ratios. For example, one such chelate is a tetradentate β-diketonate-europium chelate [Ref: Yuan, J. and Matsumoto, K.; Anal. Chem. 70, 596-601 (1998)]. In addition to the fluorescent labels described above, other labels that are suitable for use in the present invention may be described in U.S. Pat. No. 6,030,840 to Mullinax, et al.; U.S. Pat. No. 5,585,279 to Davidson; U.S. Pat. No. 5,573,909 to Singer. et al.; U.S. Pat. No. 6,242,268 to Wieder, et al.; and U.S. Pat. No. 5,637,509 to Hemmila, et al., which are incorporated herein in their entirety by reference thereto for all purposes.

Detectable substances, such as described above, may be used alone or in conjunction with a particle (sometimes referred to as "beads" or "microbeads"). For instance, naturally occurring particles, such as nuclei, mycoplasma, plasmids, plastids, mammalian cells (e.g., erythrocyte ghosts), unicellular microorganisms (e.g., bacteria), polysaccharides (e.g., agarose), etc., may be used. Further, synthetic particles may also be utilized. For example, in one embodiment, latex microparticles that are labeled with a fluorescent or colored dye are utilized. Although any synthetic particle may be used in the present invention, the particles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. Other suitable particles may be described in U.S. Pat. No. 5,670,381 to Jou, et al. and U.S. Pat. No. 5,252,459 to Tarcha, et al. Commercially available examples of suitable fluorescent particles include fluorescent carboxylated microspheres sold by Molecular Probes, Inc. under the trade names "FluoSphere" (Red 580/605) and "TransfluoSphere" (543/620), as well as "Texas Red" and 5- and 6-carboxytetramethylrhodamine, which are also sold by Molecular Probes, Inc. In addition, commercially available examples of suitable colored, latex microparticles include carboxylated latex beads sold by Bang's Laboratory, Inc. Metallic particles (e.g., gold particles) may also be utilized in the present invention.

When utilized, the shape of the particles may generally vary. In one particular embodiment, for instance, the particles are spherical in shape. However, it should be understood that other shapes are also contemplated by the present invention, such as plates, rods, discs, bars, tubes, irregular shapes, etc. In addition, the size of the particles may also vary. For instance, the average size (e.g., diameter) of the particles may range from about 0.1 nanometers to about 1,000 microns, in some embodiments, from about 0.1 nanometers to about 100 microns, and in some embodiments, from about 1 nanometer to about 10 microns. For instance, "micron-scale" particles are often desired. When utilized, such "micron-scale" particles may have an average size of from about 1 micron to about 1,000 microns, in some embodiments from about 1 micron to about 100 microns, and in some embodiments, from about 1 micron to about 10 microns. Likewise, "nano-scale" particles may also be utilized. Such "nano-scale" particles may have an average size of from about 0.1 to about 10 nanometers, in some embodiments from about 0.1 to about 5 nanometers, and in some embodiments, from about 1 to about 5 nanometers.

In some instances, it may be desired to modify the detection probes in some manner so that they are more readily able to bind to the analyte. In such instances, the detection probes may be modified with certain specific binding members that are adhered thereto to form conjugated probes. Specific binding members generally refer to a member of a specific binding pair, i.e., two different molecules where one of the molecules chemically and/or physically binds to the second molecule. For instance, immunoreactive specific binding members may include antigens, haptens, aptamers, antibodies (primary or secondary), and complexes thereof, including those formed by recombinant DNA methods or peptide synthesis. An antibody may be a monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art. Other common specific binding pairs include but are not limited to, biotin and avidin (or derivatives thereof), biotin and streptavidin, carbohydrates and lectins, complementary nucleotide sequences (including probe and capture nucleic acid sequences used in DNA hybridization assays to detect a target nucleic acid sequence), complementary peptide sequences including those formed by recombinant methods, effector and receptor molecules, hormone and hormone binding protein, enzyme cofactors and enzymes, enzyme inhibitors and enzymes, and so forth. Furthermore, specific binding pairs may include members that are analogs of the original specific binding member. For example, a derivative or fragment of the analyte, i.e., an analyte-analog, may be used so long as it has at least one epitope in common with the analyte.

The specific binding members may generally be attached to the detection probes using any of a variety of well-known techniques. For instance, covalent attachment of the specific binding members to the detection probes (e.g., particles) may be accomplished using carboxylic, amino, aldehyde, bromoacetyl, iodoacetyl, thiol, epoxy and other reactive or linking functional groups, as well as residual free radicals and radical cations, through which a protein coupling reaction may be accomplished. A surface functional group may also be incorporated as a functionalized co-monomer because the surface of the detection probe may contain a relatively high surface concentration of polar groups. In addition, although detection probes are often functionalized after synthesis, such as with poly(thiophenol), the detection probes may be capable of direct covalent linking with a protein without the need for further modification. For example, in one embodiment, the first step of conjugation is activation of carboxylic groups on the probe surface using carbodiimide. In the second step, the activated carboxylic acid groups are reacted with an amino group of an antibody to form an amide bond. The activation and/or antibody coupling may occur in a buffer, such as phosphate-buffered saline (PBS) (e.g., pH of 7.2) or 2-(N-morpholino)ethane sulfonic acid (MES) (e.g., pH of 5.3). The resulting detection probes may then be contacted with ethanolamine, for instance, to block any remaining activated sites. Overall, this process forms a conjugated detection probe, where the antibody is covalently attached to the probe. Besides covalent bonding, other attachment techniques, such as physical adsorption, may also be utilized in the present invention.

Referring again to FIG. 1, the chromatographic medium 23 also defines a detection zone 31 within which is immobilized a receptive material that is capable of binding to the conjugated detection probes. For example, in some embodiments, the receptive material may be a biological receptive material. Such biological receptive materials are well known in the art and may include, but are not limited to, antigens, haptens, protein A or G, neutravidin, avidin, streptavidin, captavidin, primary or secondary antibodies (e.g., polyclonal, monoclonal, etc.), and complexes thereof. In many cases, it is desired that these biological receptive materials are capable of binding to a specific binding member (e.g., antibody) present on the detection probes. The receptive material serves as a stationary binding site for complexes formed between the analyte and conjugated detection probes. Specifically, analytes, such as antibodies, antigens, etc., typically have two or more binding sites (e.g., epitopes). Upon reaching the detection zone 31, one of these binding sites is occupied by the specific binding member of the conjugated probe. However, the free binding site of the analyte may bind to the immobilized receptive material. Upon being bound to the immobilized receptive material, the complexed probes form a new ternary sandwich complex.

The detection zone 31 may generally provide any number of distinct detection regions so that a user may better determine the concentration of a particular analyte within a test sample. Each region may contain the same receptive materials, or may contain different receptive materials for capturing multiple analytes. For example, the detection zone 31 may include two or more distinct detection regions (e.g., lines, dots, etc.). The detection regions may be disposed in the form of lines in a direction that is substantially perpendicular to the flow of the test sample through the assay device 20. Likewise, in some embodiments, the detection regions may be disposed in the form of lines in a direction that is substantially parallel to the flow of the test sample through the assay device 20.

Although the detection zone 31 provides accurate results for detecting an analyte, it is sometimes difficult to determine the relative concentration of the analyte within the test sample under actual test conditions. Thus, the assay device 20 may also include a calibration zone 32. In this embodiment, the calibration zone 32 is positioned downstream from the detection zone 31. Alternatively, however, the calibration zone 32 may also be positioned upstream from the detection zone 31. The calibration zone 32 may be provided with a receptive material that is capable of binding to calibration probes or uncomplexed detection probes that pass through the length of the chromatographic medium 23. When utilized, the calibration probes may be formed from the same or different materials as the detection probes. Generally speaking, the calibration probes are selected in such a manner that they do not bind to the receptive material at the detection zone 31.

The receptive material of the calibration zone 32 may be the same or different than the receptive material used in the detection zone 31. For example, in one embodiment, the receptive material is a biological receptive material. In addition, it may also be desired to utilize various non-biological materials for the receptive material of the calibration zone 32. The polyelectrolytes may have a net positive or negative charge, as well as a net charge that is generally neutral. For instance, some suitable examples of polyelectrolytes having a net positive charge include, but are not limited to, polylysine (commercially available from Sigma-Aldrich Chemical Co., Inc. of St. Louis, Mo.), polyethylenimine; epichlorohydrin-functionalized polyamines and/or polyamidoamines, such as poly(dimethylamine-co-epichlorohydrin); polydiallyldimethyl-ammonium chloride; cationic cellulose derivatives, such as cellulose copolymers or cellulose derivatives grafted with a quaternary ammonium water-soluble monomer; and so forth. In one particular embodiment, CelQuat® SC-230M or H-100 (available from National Starch & Chemical, Inc.), which are cellulosic derivatives containing a quaternary ammonium water-soluble monomer, may be utilized. Moreover, some suitable examples of polyelectrolytes having a net negative charge include, but are not limited to, polyacrylic acids, such as poly(ethylene-co-methacrylic acid, sodium salt), and so forth. It should also be understood that other polyelectrolytes may also be utilized in the present invention, such as amphiphilic polyelectrolytes (i.e., having polar and non-polar portions). For instance, some examples of suitable amphiphilic polyelectrolytes include, but are not limited to, poly(styryl-b-N-methyl 2-vinyl pyridinium iodide) and poly (styryl-b-acrylic acid), both of which are available from Polymer Source, Inc. of Dorval, Canada. Further examples of internal calibration systems that utilize polyelectrolytes are described in more detail in U.S. Patent App. Publication No. 2003/0124739 to Song, et al., which is incorporated herein in it entirety by reference thereto for all purposes.

In some cases, the chromatographic medium 23 may also define a control zone (not shown) that gives a signal to the user that the assay is performing properly. For instance, the control zone (not shown) may contain an immobilized receptive material that is generally capable of forming a chemical and/or physical bond with probes or with the receptive material immobilized on the probes. Some examples of such receptive materials include, but are not limited to, antigens, haptens, antibodies, protein A or G, avidin, streptavidin, secondary antibodies, and complexes thereof. In addition, it may also be desired to utilize various non-biological materials for the control zone receptive material. For instance, in some embodiments, the control zone receptive material may also include a polyelectrolyte, such as described above, that may bind to uncaptured probes. Because the receptive material at the control zone is only specific for probes, a signal forms regardless of whether the analyte is present. The control zone may be positioned at any location along the medium 23, but is typically positioned upstream from the detection zone 31.

Various formats may be used to test for the presence or absence of an analyte using the assay device 20. For instance, a "sandwich" format typically involves mixing the test sample with detection probes conjugated with a specific binding member (e.g., antibody) for the analyte to form complexes between the analyte and the conjugated probes. These complexes are then allowed to contact a receptive material (e.g., antibodies) immobilized within the detection zone. Binding occurs between the analyte/probe conjugate complexes and the immobilized receptive material, thereby localizing "sandwich" complexes that are detectable to indicate the presence of the analyte. This technique may be used to obtain quantitative or semi-quantitative results. Some examples of such sandwich-type assays are described by U.S. Pat. No. 4,168,146 to Grubb, et al. and U.S. Pat. No. 4,366, 241 to Tom, et al., which are incorporated herein in their entirety by reference thereto for all purposes. In a competitive assay, the labeled probe is generally conjugated with a molecule that is identical to, or an analog of, the analyte. Thus, the labeled probe competes with the analyte of interest for the available receptive material. Competitive assays are typically used for detection of analytes such as haptens, each hapten being monovalent and capable of binding only one antibody molecule. Examples of competitive immunoassay devices are described in U.S. Pat. No. 4,235,601 to Deutsch, et al., U.S. Pat. No. 4,442,204 to Liotta, and U.S. Pat. No. 5,208,535 to Buechler, et al., which are incorporated herein in their entirety by reference thereto for all purposes. Various other device configurations and/or assay formats are also described in U.S. Pat. No. 5,395,754 to Lambotte, et al.; U.S. Pat. No. 5,670, 381 to Jou, et al.; and U.S. Pat. No. 6,194,220 to Malick, et al., which are incorporated herein in their entirety by reference thereto for all purposes.

II. Optical Detection System

Regardless of the particular type of assay device utilized, an optical detection system is employed in accordance with the present invention to detect the presence or absence of an analyte. The optical detection system utilized in the present invention employs transmission-based measurements to minimize signal interference and to reduce the need for expensive and complex instruments. Thus, the resulting system is inexpensive, easy to use, and has an improved signal-to-noise ratio.

Referring again to FIG. 1, for example, the illustrated detection system employs an illumination source 52 and a detector 54. As shown, the detector 54 is positioned adjacent to the support 21 and the illumination source 52 is positioned adjacent to the second surface 14 of the chromatographic medium 23. Likewise, the detector 54 may be positioned adjacent to the second surface 14 of the chromatographic medium 23 and the illumination source 52 may be positioned adjacent to the support 21. Thus, the illumination source 52 may emit light simultaneously onto the detection and calibration zones 31 and 32, and the detector 54 may likewise also simultaneously receive a detection signal from the probes at the detection and calibration zones 31 and 32. Alternatively, the illumination source 52 may be constructed to successively emit light onto the detection zone 31 and the calibration zone 32. In addition, a separate illumination source and/or detector (not shown) may also be used for the calibration zone 32.

Figures 3A, 3B, 3C, 3D:
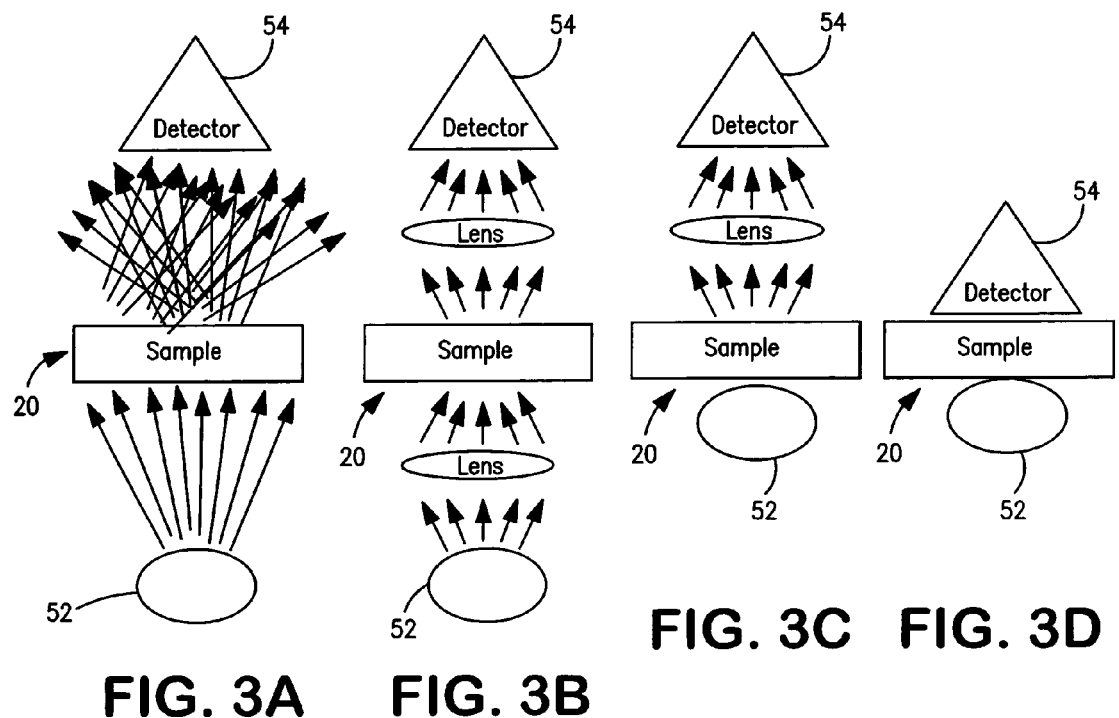
FIG. 3a illustrates an embodiment in which the illumination source and detector are spaced relatively distant from the assay device.
FIG. 3b illustrates the embodiment of FIG. 3a in which an illumination lens and a detection lens are also used to focus light to and from the assay device.
FIG. 3c illustrates the embodiment of FIG. 3b in which the illumination lens is removed and the illumination source is moved closer to the assay device.
FIG. 3d illustrates the embodiment of FIG. 3c in which the detection lens is removed and the detector is moved closer to the assay device.

To improve the signal-to-noise ratio of the optical detection system without the need for certain types of complex and expensive optical components, such as lenses or other light guiding elements, the distance of the illumination source 52 and/or detector 54 from the assay device 20 is typically minimized. For instance, as shown in FIG. 3a, light (indicated by directional arrows) traveling a relatively large distance tends to diffuse, thereby causing some photons to miss the test sample or the detector 54. To reduce light scattering, lenses may be employed to focus the light in the desired direction, such as shown in FIG. 3b. However, as shown in FIGS. 3c and 3d, the need for such expensive and complex equipment may be reduced by simply moving the illumination source 52 and/or detector 54 closer to the assay device 20. The use of a shorter light path results in less diffusion of the light. For example, FIG. 3c illustrates an embodiment in which the illumination source 52 is positioned closer to the assay device 20, and FIG. 3d illustrates an embodiment in which both the illumination source 52 and detector 54 are positioned closer to the assay device 20. Thus, in some embodiments, the illumination source 52 and/or detector 54 may be positioned less than about 5 millimeters, in some embodiments less than about 3 millimeters, and in some embodiments, less than about 2 millimeters from the assay device 20. For example, the illumination source 52 may be laminated directly to the support 21. Likewise, as will be discussed in more detail below, the illumination source 52 and/or detector 54 may, in some cases, directly contact the chromatographic medium 23. For example, the illumination source 52 may carry the medium 23, thereby also functioning as its support. In other cases, however, it may be desired to keep the illumination source 52 and/or detector 54 at a distance that is large enough to avoid contamination of any biological reagents. For example, the illumination source 52 and/or detector 54 may sometimes be positioned at a distance of from about 1 to about 3 millimeters from the assay device 20.

Generally speaking, the illumination source 52 may be any device known in the art that is capable of providing electromagnetic radiation at a sufficient intensity to cause probes to produce a detection signal. The electromagnetic radiation may include light in the visible or near-visible range, such as infrared or ultraviolet light. For example, suitable illumination sources that may be used in the present invention include, but are not limited to, light emitting diodes (LED), flashlamps, cold-cathode fluorescent lamps, electroluminescent lamps, and so forth. The illumination may be multiplexed and/or collimated. In some cases, the illumination may be pulsed to reduce any background interference. Further, illumination may be continuous or may combine continuous wave (CW) and pulsed illumination where multiple illumination beams are multiplexed (e.g., a pulsed beam is multiplexed with a CW beam), permitting signal discrimination between a signal induced by the CW source and a signal induced by the pulsed source. For example, in some embodiments, LEDs (e.g., aluminum gallium arsenide red diodes, gallium phosphide green diodes, gallium arsenide phosphide green diodes, or indium gallium nitride violet/blue/ultraviolet (UV) diodes) are used as the pulsed illumination source 52. One commercially available example of a suitable UV LED excitation diode suitable for use in the present invention is Model NSHU550E (Nichia Corporation), which emits 750 to 1000 microwatts of optical power at a forward current of 10 milliamps (3.5-3.9 volts) into a beam with a full-width at half maximum of 10 degrees, a peak wavelength of 370-375 nanometers, and a spectral half-width of 12 nanometers.

In some cases, the illumination source 52 may provide diffuse illumination to the assay device 20. In this manner, the reliance on certain external optical components, such as diffusers, may be virtually eliminated. For example, in some embodiments, an array of multiple point light sources (e.g., LEDs) may simply be employed to provide relatively diffuse illumination to the device 20. Another particularly desired illumination source that is capable of providing diffuse illumination in a relatively inexpensive manner is an electroluminescent (EL) device. An EL device is generally a capacitor structure that utilizes a luminescent material (e.g., phosphor particles) sandwiched between electrodes, at least one of which is transparent to allow light to escape. Application of a voltage across the electrodes generates a changing electric field within the luminescent material that causes it to produce light.

Generally speaking, any known EL device may be employed as the illumination source 52. For example, EL devices that employ "inorganic" or "organic" luminescent materials may be utilized in the present invention. Suitable "organic" EL devices include low and high molecular weight devices. Likewise, suitable inorganic EL devices include dispersion and thin-film phosphors. Dispersion EL devices generally contain a dispersion of powder luminescent material in a binder, which is sandwiched between electrode layers. On the other hand, thin-film EL devices include a luminescent thin film that is sandwiched between a pair of insulating thin films and a pair of electrode layers, and is disposed on an electrically insulating substrate. Although certainly not required, the dispersion-type EL devices are particularly desired in certain embodiments of the present invention due to their relatively low cost and ease of manufacture.

Figure 2:
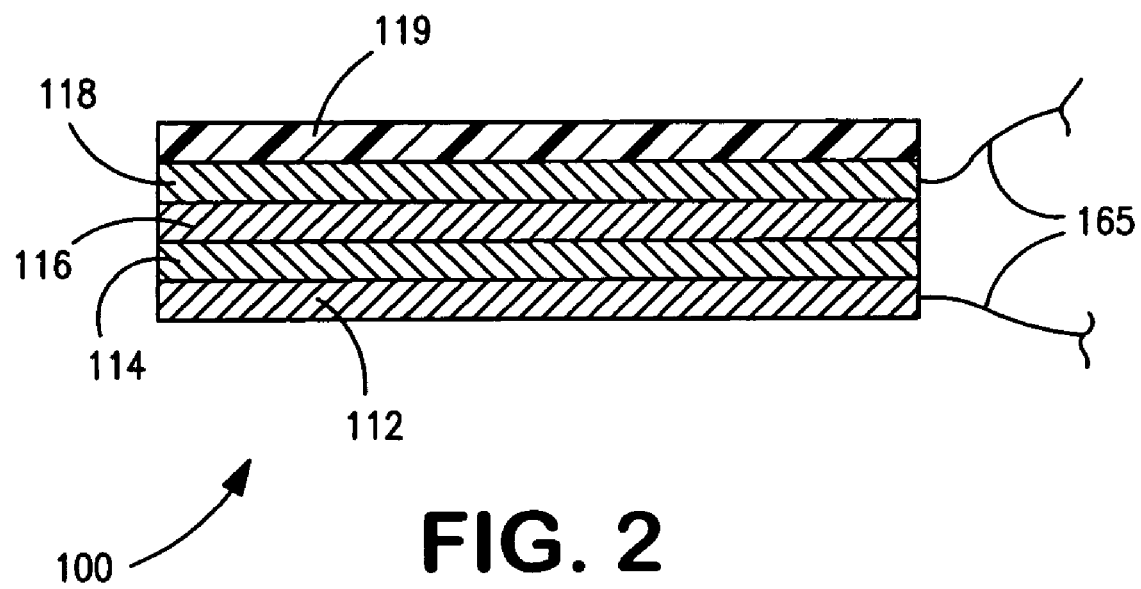
FIG. 2 is a cross-sectional view of an electroluminescent (EL) device that may be used in one embodiment of the present invention.

Referring to FIG. 2, for instance, one embodiment of a dispersion-type EL device 100 that may be used in the present invention is illustrated. As shown, the EL device 100 has a cathode 112, a dielectric layer 114, a luminescent layer 116, an anode 118, and a film 119. Additional water-impervious protective layers (not shown) may optionally be applied to the cathode 112 and film 119 if desired. Leads 165 are electrically attached to the respective cathode and anode layers 112 and 118. The cathode 112 may be formed from a metal (including metalloids) or alloys thereof (including intermetallic compounds). Examples of suitable materials for forming the cathode 112 include, but are not limited to, carbon; metals, such as aluminum, gold, silver, copper, platinum, palladium, iridium, and alloys thereof; and so forth. The thickness of the cathode 112 may generally vary, and may be deposited onto an electrically insulating substrate (not shown). The substrate, for instance, may be formed from ceramic materials, such as alumina ($Al_2O_3$), quartz glass ($SiO_2$), magnesia (MgO), forsterite ($2MgO.SiO_2$), steatite ($MgO.SiO_2$), mullite ($3Al_2O_3.2SiO_2$), beryllia (BeO), zirconia ($ZrO_2$), aluminum nitride (AlN), silicon nitride (SiN), silicon carbide (SiC), glass, heat resistant glass, and so forth. In addition, polymeric materials may also be used to form the substrate, such as, polypropylene, polyethylene terephthalate, polyvinyl chloride, polymethylmethacrylate, and so forth.

The dielectric layer 114 is disposed on the cathode 112. The material of which the dielectric layer 114 is formed may generally vary as is well known to those skilled in the art. For example, suitable materials include, but are not limited to, perovskite structure dielectric and ferroelectric materials, such as $BaTiO_3$, $(Ba_xCa_{1-x})TiO_3$, $(Ba_xSr_{1-x})TiO_3$, $PbTiO_3$ and $Pb(Zr_xTi_{1-x})O_3$ (known as "PZT"); complex perovskite relaxation type ferroelectric materials, such as $Pb(Mg_{1/3}Nb_{2/3})O_3$; bismuth layer compounds, such as $Bi_4Ti_3O_{12}$ and $SrBi_2Ta_2O_9$; and tungsten bronze type ferroelectric materials, such as $(Sr_xBa_{1-x})Nb_2O_6$ and $PbNb_2O_6$. Still other suitable dielectric materials for use in the dielectric layer 114 may include dielectric material, such as $SiO_2$, SiN, SiON, $ZrO_2$, $Al_2O_3$, $Al_3N_4$, $Y_2O_3$, $Ta_2O_5$, and so forth. In one particular embodiment, the dielectric layer 114 is formed from barium titanate ($BaTiO_3$).

The dielectric layer 114 may be formed using any of a variety of techniques known to those skilled in the art. For example, the dielectric material used to form the layer 114 may first be admixed with a suitable solvent. Such solvents may include, for instance, glycol ethers, alkyl ketones and aromatic solvents. Suitable glycol ethers may include propylene glycol methyl ether, dipropylene glycol methyl ether, tripropylene glycol methyl ether, ethylene glycol ethyl ether, diethylene glycol butyl ether, and so forth. Suitable alkyl ketones may include lower alkyl ketones, such as acetone, methyl ethyl ketone, ethyl ketone and methylisobutyl ketone, and so forth. Suitable aromatic solvents may include toluene, xylene, and so forth. In one embodiment, barium titanate is added to a solvent in an amount from about 70% to about 90% by weight. The barium titanate and the solvent are then stirred together to form a homogeneous slurry.

Upon mixing with a solvent, the dielectric material may also be mixed with a binder. For example, in some embodiments, the binder is added in an amount from about 10 to about 30 parts of the slurry. Suitable binders are well known and include, for instance, epoxy resins, polystyrene, polyethylene, polyvinyl butyral, polyvinyl chloride, polyvinyl acetate, polyvinyl alcohol, polyesters, polyamides, polyacrylonitrile, polyacrylate, polymethylmethacrylate and the like. In some embodiments, the binder is an adhesive thermoplastic reaction product of phenols and an excess of an epihalohydrin. Suitable phenols include bisphenol A, dichlorobisphenol A, tetrachlorobisphenol A, tetrabromobisphenol A, bisphenol F and bisphenol ACP. The reaction is carried out in the presence of a glycol ether or other suitable solvent. To this reaction product is added a resin such as a urethane or an epoxy resin in the range of from about 5 to 6 parts of resin to about 1 part of the epihalohydrin/phenol reaction product. Such binders are described in more detail in U.S. Pat. No. 4,560,902 to Kardon and U.S. Pat. No. 5,352,951 to Kardon, et al., which are incorporated herein in their entirety by reference thereto for all purposes.

If desired, water may be added to the binder system at this step or following assembly of the EL device 100. The water may be stirred into the slurry before or after removal of the solvent. The amount of water added to the binder will vary somewhat in accordance with the amount of water the particular binder employed can absorb. For instance, at least about 1 part per million ("ppm") (0.0001%) of water may be present and up to the maximum amount of water the binder will absorb. Cyanoethyl polyvinyl alcohol binders, for example, typically absorb a maximum of about 40,000 ppm (4.0%) of water. Cyanoalkylated pullulan binders, on the other hand, typically absorb a maximum of about 100,000 ppm (10.0%) of water. However, in most cases, the amount of water added to the binder is from about 500 ppm (0.05%) to about 20,000 ppm (2.0%). The thickness of the resultant barium titanate/resin binder layer 114 is typically from about 0.2 to about 6 mils.

Referring again to FIG. 2, the EL device 100 also includes a luminescent layer 116 disposed on the dielectric layer 114. The material of which the luminescent layer 116 may include phosphor particles. Suitable phosphor particles may include a variety of metal oxide, sulfide, fluoride, and silicate compounds. For example, such phosphor particles may include manganese- and arsenic-activated zinc silicate (P39 phosphor), titanium-activated zinc silicate, manganese-activated zinc silicate (P1 phosphor), cerium-activated yttrium silicate (P47 phosphor), manganese-activated magnesium silicate (P13 phosphor), lead- and manganese-activated calcium silicate (P25 phosphor), terbium-activated yttrium silicate, terbium-activated yttrium oxide, terbium-activated yttrium aluminum oxide, terbium-activated gadolinium oxide, terbium-activated yttrium aluminum gallium oxide, europium-activated yttrium oxide, europium-activated yttrium vanadium oxide, europium-activated yttrium oxysulfide, manganese-activated zinc sulfide, cesium-activated strontium sulfide, thulium-activated zinc sulfide, samarium-activated zinc sulfide, europium-activated calcium sulfide, terbium-activated zinc-sulfide, and cesium-activated calcium sulfide, and so forth.

The color emitted by the phosphor particles can be defined during the manufacture of the phosphor or by blending phosphors of different colors to achieve composite color. Some specific examples of suitable phosphors include manganese-activated zinc sulfide (yellowish orange light emission), cesium-activated strontium sulfide (blue light emission), thulium-activated zinc sulfide (blue light emission), samarium-activated zinc sulfide (red light emission), europium-activated calcium sulfide (red light emission), terbium-activated zinc-sulfide (green light emission), and cesium-activated calcium sulfide (green light emission).

Phosphor particles typically have an average size of less than about 15 micrometers, in some embodiments less than about 10 micrometers, and in some embodiments, less than about 5 micrometers. The luminescent layer 116 may be formed using any of a variety of techniques known to those skilled in the art. For example, the encapsulated phosphor particles may be admixed with a solvent, such as described above. The amount of phosphor particles added to the solvent may range, for instance, from about 60% to about 95%, and in some embodiments, from about 75% to about 85% by weight of the mixture. Likewise, after mixing, a binder, such as described above, is also mixed with the phosphor particle slurry. The binder is typically present in an amount of from about 5 to about 40 parts. If desired, the phosphor particles may also be encapsulated within a protective material to form a water barrier as is well known in the art. Suitable protective materials for encapsulating the phosphor particles include, for instance, liquid crystals, polymeric binders, ceramic materials (e.g., colloidal silica, alumina, etc.), and so forth. Encapsulation techniques are described in more detail in U.S. Pat. No. 4,097,776 to Allinikov; U.S. Pat. No. 4,513,023 to Warv; U.S. Pat. No. 4,560,902 to Kardon; and U.S. Pat. No. 5,352,951 to Kardon, et al., which are incorporated herein in their entirety by reference thereto for all purposes.

The phosphor particles preferably are deposited in a smooth, homogeneous layer by any of a variety of techniques known to one of skill in the art. Such techniques include settling techniques, slurry methods (such as screen printing, spin coating, and spin casting), electrophoresis, or dusting methods (such as electrostatic dusting, "phototacky" methods, and high pressure dusting). Settling techniques and slurry methods involve forming a dispersion of the phosphor particles in a suitable liquid medium. One particularly desired deposition method is screen printing. A suitable thickness for the phosphor/binder layer 116 when dried is about 0.2 to about 6 mils.

In addition to the layers mentioned above, the EL device 100 also includes an anode 118 formed on a film 119, both of which are disposed over the luminescent layer 116. Desirably, the materials used for the layers 118 and 119 are optically transparent. For example, the anode 118 may be formed from a inorganic conductive oxide, such as indium oxide, indium tin oxide (ITO), tin oxide, and antimony tin oxide. In one embodiment, an indium tin oxide (ITO) layer is utilized that has a thickness of about 0.2 to 1 micrometers. Likewise, a suitable material for use as the film 119 may be a polymer film (e.g., polyester). It should be understood that the embodiments described above are merely exemplary, and that any other known EL device may generally be used in the present invention. For instance, other suitable EL devices are described in U.S. Pat. No. 6,004,686 to Rasmussen, et al.; U.S. Pat. No. 6,432,516 to Terasaki, et al.; U.S. Pat. No. 6,602,618 to Watanabe, et al.; U.S. Pat. No. 6,479,930 to Tanabe, et al.; U.S. Pat. No. 6,723,192 to Nagano, et al.; and U.S. Pat. No. 6,734,469 to Yano, et al., as well as U.S. Patent Application Publication Nos. 2003/0193289 to Shirakawa, et al.; 2004/0119400 to Takahashi, et al., and 2004/0070195 to Nelson, et al., all of which are incorporated herein in their entirety by reference thereto for all purposes.

When utilized as the illumination source 52 (FIG. 1), EL devices may provide a variety of benefits for the optical detection system. For instance, unlike point light sources used with many conventional optical detection systems (e.g. LEDs), EL devices emit relatively homogeneous and diffuse light, and may thus provide uniform illumination. This may eliminate the need for additional diffusers often required in other point-source illumination systems. In addition, the light intensity emitted by EL device may be easily controlled by simply varying the voltage or the frequency of the drive signal. Thus, an EL device allows for the use of optical readers that are relatively simple, portable, and inexpensive.

In FIG. 1, the illumination source 52 is shown as a component that is separate from the assay device 20. However, the present invention also contemplates embodiments in which the illumination source is integral with the assay device 20. For example, in some embodiments, the support 21 is an EL device that functions simultaneously as a light source for the optical detection system and as a physical carrier for the chromatographic medium 23. The use of an EL device as the support 21 provides a substantial benefit to the resulting optical detection system by eliminating the need for additional light sources, which are often costly and lead to overly complex and space-consuming systems. That is, the EL device may be laminated to the chromatographic medium 23 and simultaneously function as the support 21 and light source for the optical detection system. The EL device may be selected to possess a certain degree of flexibility that allows it to be readily manipulated and/or cut into the desired shape and size for the assay device 20. One commercially available EL device that has enough strength and flexibility for use as the support 21 is a lamp kit available from Graphic Solutions Int'l, LLC of Burr Ridge, Ill. under the name "Proto-Kut."

Figure 4:
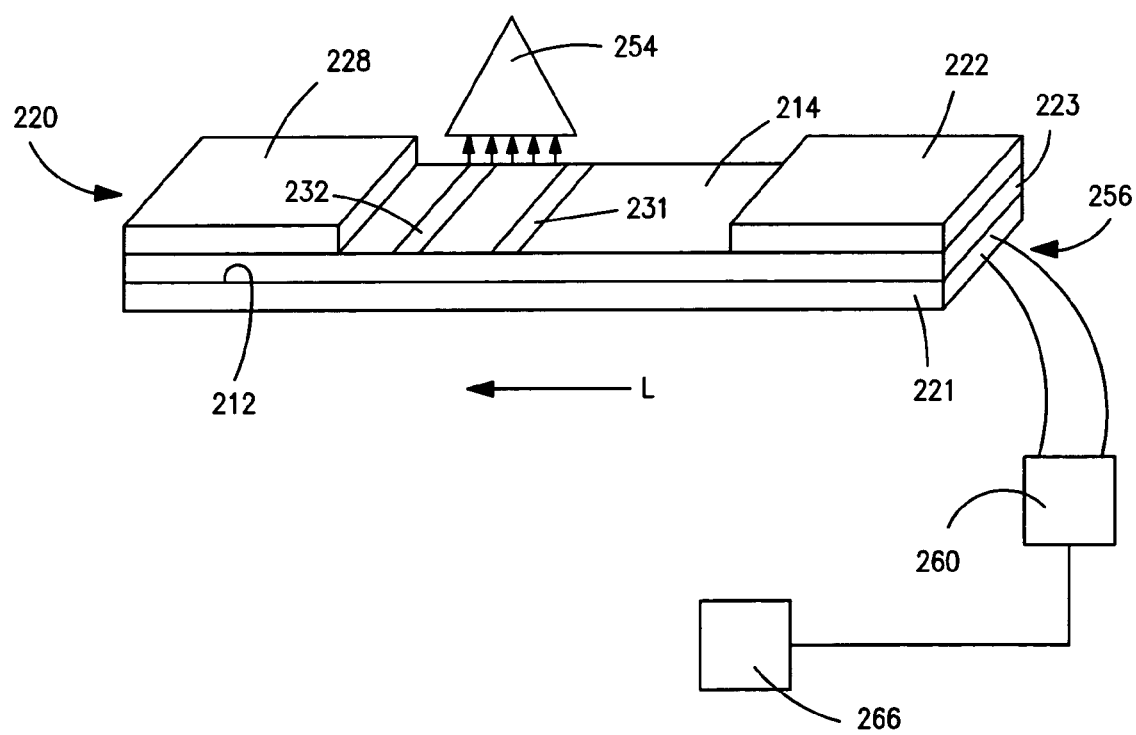
FIG. 4 is a perspective view of another embodiment of an optical detection system of the present invention, which employs an EL illumination source.

One particular embodiment of the present invention in which an EL device is employed as the support for the assay device is shown in FIG. 4. Specifically, an assay device 220 is depicted that includes a chromatographic medium 223, an EL device 221, an absorbent pad 228, and a conjugate pad 222. The medium 223 has a first surface 212 and a second surface 214, wherein the first surface 212 is positioned adjacent to the EL device 221. A detection zone 231 and calibration zone 232 are defined by the medium 223 for providing detection and calibration signals. Further, a detector 254 positioned adjacent to the second surface 214 of the medium 223. In this particular embodiment, the EL device 221 functions as both the illumination source and the support for the medium 223. Leads 256 for the EL device 221 are connected to a driver circuit 260 via wiring, which in turn, is connected to a power source 266. The details of the driver circuit 260 and power source 266 depend on the requirements of the particular EL device. For example, because the EL device 221 may be relatively small due to the corresponding small size of the assay device 220, a low voltage circuit and battery power source may be employed to reduce the cost and complexity of the system. However, higher voltage circuits may also be used, such as a driver circuit that converts DC voltage into an AC output for driving the EL device 221. Such AC inverters may generate around 60 to 300 volts AC at 50 to 5000 Hertz. Driver circuits suitable for this purpose are commercially available.

Referring again to FIG. 1, the detector 54 may generally be any device known in the art that is capable of sensing an optical signal. For instance, the detector 54 may be an electronic imaging detector that is configured for spatial discrimination. Some examples of such electronic imaging sensors include high speed, linear charge-coupled devices (CCD), charge-injection devices (CID), complementary-metal-oxide-semiconductor (CMOS) devices, and so forth. Such image detectors, for instance, are generally two-dimensional arrays of electronic light sensors, although linear imaging detectors (e.g., linear CCD detectors) that include a single line of detector pixels or light sensors, such as, for example, those used for scanning images, may also be used. Each array includes a set of known, unique positions that may be referred to as "addresses." Each address in an image detector is occupied by a sensor that covers an area (e.g., an area typically shaped as a box or a rectangle). This area is generally referred to as a "pixel" or pixel area. A detector pixel, for instance, may be a CCD, CID, or a CMOS sensor, or any other device or sensor that detects or measures light. The size of detector pixels may vary widely, and may in some cases have a diameter or length as low as 0.2 micrometers.

In other embodiments, the detector 54 may be a light sensor that lacks spatial discrimination capabilities. For instance, examples of such light sensors may include photomultiplier devices, photodiodes, such as avalanche photodiodes or silicon photodiodes, and so forth. Silicon photodiodes are sometimes advantageous in that they are inexpensive, sensitive, capable of high-speed operation (short risetime/high bandwidth), and easily integrated into most other semiconductor technology and monolithic circuitry. In addition, silicon photodiodes are physically small, which enables them to be readily incorporated into a system for use with a membrane-based device. If silicon photodiodes are used, then the wavelength range of the emitted signal may be within their range of sensitivity, which is 400 to 1100 nanometers. Another suitable detector is a CdS (cadmium sulfide) photoconductive cell, which has the advantage of having a spectral sensitivity similar to that of human vision that may make rejection of the reflected emitted radiation easier.

Although it is generally desired to limit the use of external optical components to reduce costs and complexity, such components may nevertheless be utilized in some embodiments of the present invention. If utilized, separate optical components may be used for the illumination source 52 and detector 54, or they may share common optical components. For example, optical diffusers may be utilized in the present invention to scatter light in a certain direction, such as toward and/or away from the detection zone. Optical diffusers are particularly useful in conjunction with a detection system that employs a "point" light source, such as a light-emitting diode (LED). For example, suitable optical diffusers may include diffusers that scatter light in various directions, such as ground glass, opal glass, opaque plastics, chemically etched plastics, machined plastics, and so forth. Opal glass diffusers contain a milky white "opal" coating for evenly diffusing light, thereby producing a near Lambertian source. Other suitable light-scattering diffusers include polymeric materials (e.g., polyesters, polycarbonates, etc.) that contain a light-scattering material, such as titanium dioxide or barium sulfate particles. In other embodiments, holographic diffusers may be utilized that both homogenize and impart predetermined directionality to light rays emanating from the illumination source. Such diffusers may contain a micro-sculpted surface structure that controls the direction in which light propagates. Examples of such holographic diffusers are described in more detail in U.S. Pat. No. 5,534,386 to Petersen, et al., which is incorporated herein in its entirety by reference thereto for all purposes.

Optical filters (not shown) may also be disposed adjacent to the illumination source 52 and/or detector 54. The optical filters may have high transmissibility in a desired wavelength range(s) and low transmissibility in one or more undesirable wavelength band(s) to filter out undesirable wavelengths from the illumination source 52. In luminescent detection systems, for instance, undesirable wavelength ranges may include those wavelengths that produce detectable sample autofluoresence and/or are within about 25 to about 100 nanometers of excitation maxima wavelengths and thus are potential sources of background noise from scattered excitation illumination. Several examples of optical filters that may be utilized in the present invention include, but are not limited to, dyed plastic resin or gelatin filters, dichroic filters, thin multi-layer film interference filters, plastic or glass filters, epoxy or cured transparent resin filters. In one embodiment, the detector 54 and/or illumination source 52 may be embedded or encapsulated within the filter.

In addition, a lens may also be used to collect and focus light. One particular embodiment of the present invention utilizes a micro-lens to focus light toward the test sample and/or detector 54. Suitable micro-optic lenses include, but are not limited to, gradient index (GRIN) lenses, ball lenses, Fresnel lenses, and so forth. For example, a gradient index lens is generally cylindrical, and has a refractive index that changes radially with a parabolic profile. A ball lens is generally spherical, and has a refractive index that is radially constant. Because of their relatively small size, such micro-lenses may be particularly advantageous in the present invention. Any of a variety of well-known techniques may be utilized to form the micro-lens. For example, micro-lenses may be formed by submerging a substrate (e.g., silicon or quartz) into a solution of alkaline salt so that ions are exchanged between the substrate and the salt solution through a mask formed on the substrate, thereby obtaining a substrate having a distribution of indexes of refraction corresponding to the pattern of the mask. In addition, a photosensitive monomer may be irradiated with ultraviolet rays to polymerize an irradiated portion of the photosensitive monomer. Thus, the irradiated portion bulges into a lens configuration under an osmotic pressure occurring between the irradiated portion and the non-irradiated portion. In another embodiment, a photosensitive resin may be patterned into circles, and heated to temperatures above its softening point to enable the peripheral portion of each circular pattern to sag by surface tension. This process is referred to as a "heat sagging process." Further, a lens substrate may simply be mechanically shaped into a lens. Still other suitable techniques for forming a micro-lens or other micro-optics are described in U.S. Pat. No. 5,225,935 to Watanabe, et al.; U.S. Pat. No. 5,910,940 to Guerra; and U.S. Pat. No. 6,411,439 to Nishikawa, which are incorporated herein in their entirety by reference thereto for all purposes.

Further, a mask, such as a black coating or dye, may be utilized to prevent light from passing through one or more sections of the assay device 20. Light guiding elements may also be utilized to direct light in a desired direction, such as a single optical fiber, fiber bundle, segment of a bifurcated fiber bundle, large diameter light pipe, planar waveguide, attenuated total reflectance crystal, dichroic mirror, plane mirror or other light guiding elements. Still other examples of optically functional materials that may be used in the present invention described in U.S. Pat. No. 5,827,748 to Golden; U.S. Pat. No. 6,084,683 to Bruno, et al.; U.S. Pat. No. 6,235,241 to Catt, et al.; U.S. Pat. No. 6,556,299 to Rushbrooke, et al.; and U.S. Pat. No. 6,566,508 to Bentsen, et al., which are incorporated herein in their entirety by reference thereto for all purposes.

If desired, the optical properties of the assay device itself may be selectively tailored to the optical requirements of the detection system. For example, referring again to FIG. 1, one embodiment of the present invention employs selective control of the support 21 to optimize the performance of the optical detection system. In one particular embodiment, for example, the support 21 is optically transmissive to allow for light to travel from the illumination source 52 to the detector 54. In addition, the support 21 may function as a diffuser for the illumination source 52 and/or detector 54 to improve the signal-to-noise ratio of the optical detection system. The support 21 may also function as an optical filter of the detection system. Thus, in the illustrated embodiment, light from the illumination source 52 is absorbed by probes (not shown) present at the detection zone 31 and/or calibration zone 32. The probes produce a signal that is attenuated by the optical filter before reaching the detector 54. The optical filter may, for example, have high transmissibility in the emission wavelength range(s) and low transmissibility in one or more undesirable wavelength band(s) to filter out undesirable wavelengths from the detector 54. The optical detection system may also include an additional optical filter (not shown) positioned between the illumination source 52 and the chromatographic medium 23. This additional optical filter may have high transmissibility in the excitation wavelength range(s) and low transmissibility in one or more undesirable wavelength band(s). Alternatively, an additional optical filter may be integrated into the illumination source 52 and/or detector 54. The support 21 may also posses other desirable optical qualities. For example, the support 21 may contain a mask, light guiding element, lens, etc. In some cases, when employed in the support 21, it is desired that "micro-optic" elements are utilized. Micro-optic elements generally have a size less than about 2 millimeters and are arranged in one or two dimensions. Due to their small size, micro-optic elements may be more readily utilized in the support 21.

When the support 21 is optimized for a particular optical property, the material(s) used for forming the support 21 may be selected to possess the desired optical property. Alternatively, the desired optically functional material may simply be applied to the support 21 before and/or after forming the assay device 20. Such an optically functional material may be applied to the support 21 in a variety of ways. For example, the optically functional material may simply be dyed or coated onto one or more surfaces of the support 21. When applied in this manner, the optically functional material may cover only a portion or an entire surface of the support 21. In one embodiment, for example, the optically functional material is applied to a portion of the support 21 that corresponds to the detection zone 31 and/or calibration zone 32. In this manner, the optically functional material may enhance the detection or calibration signals produced by the assay device 20 during use. Alternatively, the optically functional material may also be incorporated into the structure of the support 21. For example, internal optics may be formed using known techniques, such as embossing, stamping, molding, etc.

Figure 5A:
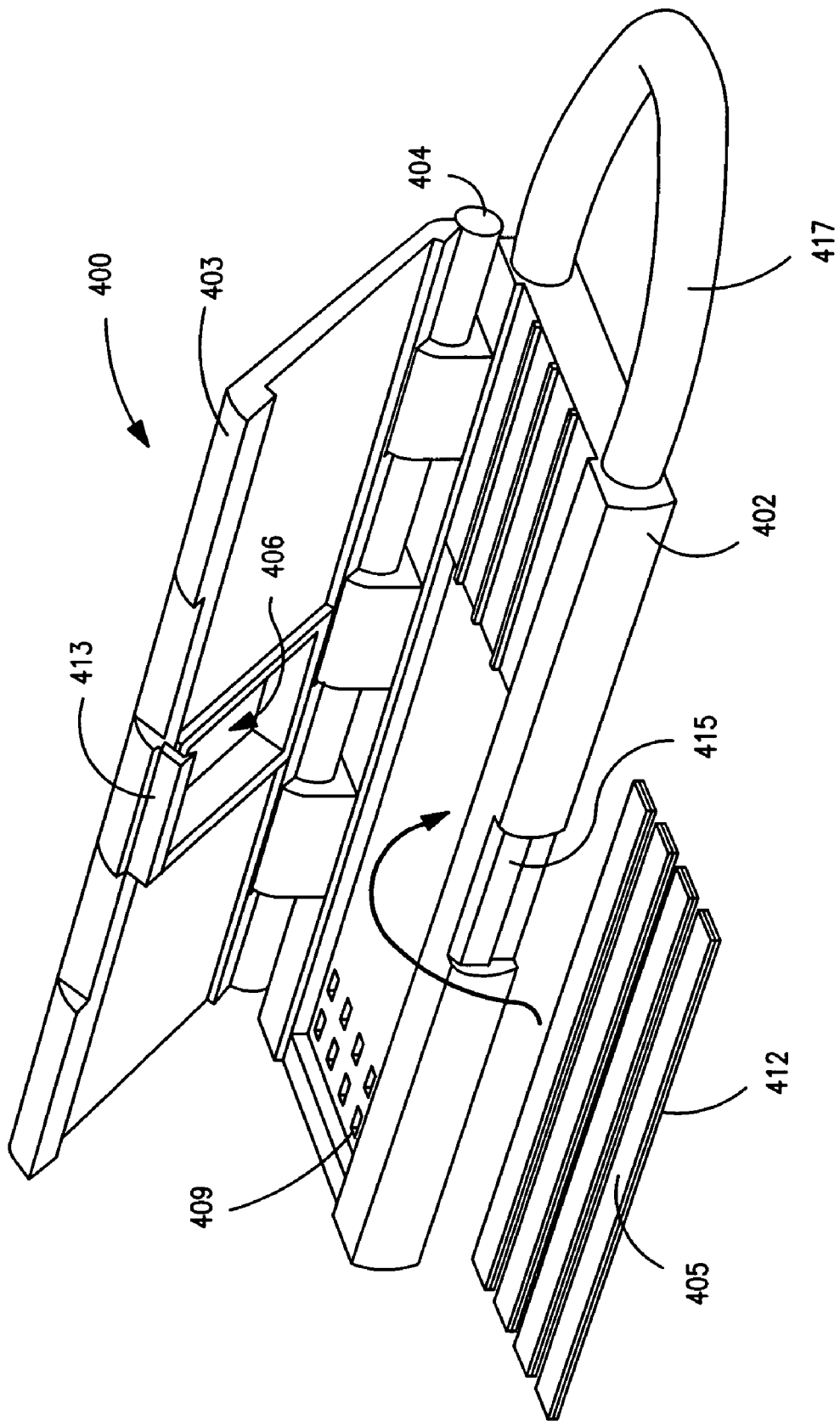
FIG. 5A shows the sample holder prior to insertion of the assay strips.
Figure 5B:
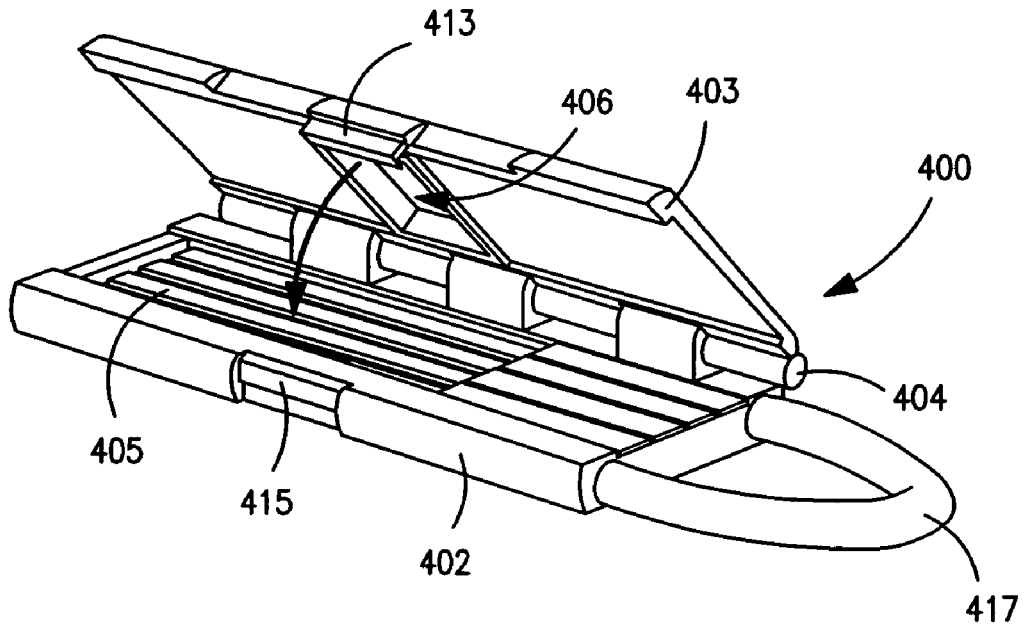
FIG. 5B shows the sample holder in its open configuration with the strips inserted.
Figure 5C:
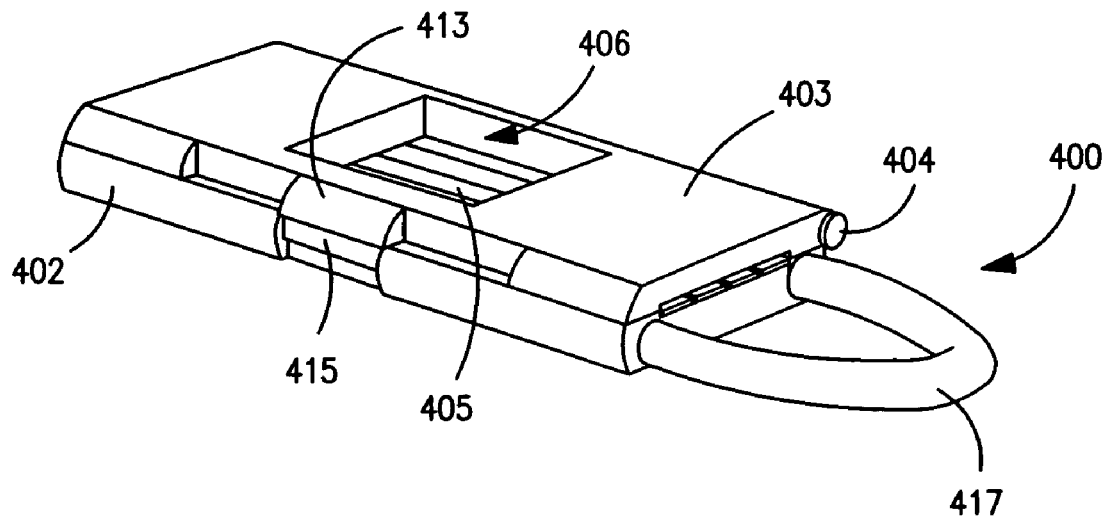
FIG. 5C shows the sample holder in its closed configuration.

In accordance with certain embodiments of the present invention, the optical detection system may also employ various other components that enhance the detection sensitivity of the analyte. For example, the detection system may sometimes employ a sample holder for the assay device. Referring to FIGS. 5-8, for example, one embodiment of an optical detection system that employs such a sample holder will now be described in more detail. FIG. 5, for instance, illustrates one embodiment of a sample holder 400 that may be employed in the optical detection system of the present invention. As shown, the sample holder 400 includes a lower portion 402 and an upper portion 403. The upper portion 403 is capable of movement about a hinge 404 so that it may be positioned in an open position (FIGS. 5A and 5B) and a closed position (FIG. 5C). Further, the sample holder 400 may include an upper latch 413 that mates with a lower latch 415 for securing the holder 400 in its closed position. A handle 417 may also be provided to allow a user to more readily grip the holder 400.

Figure 6:
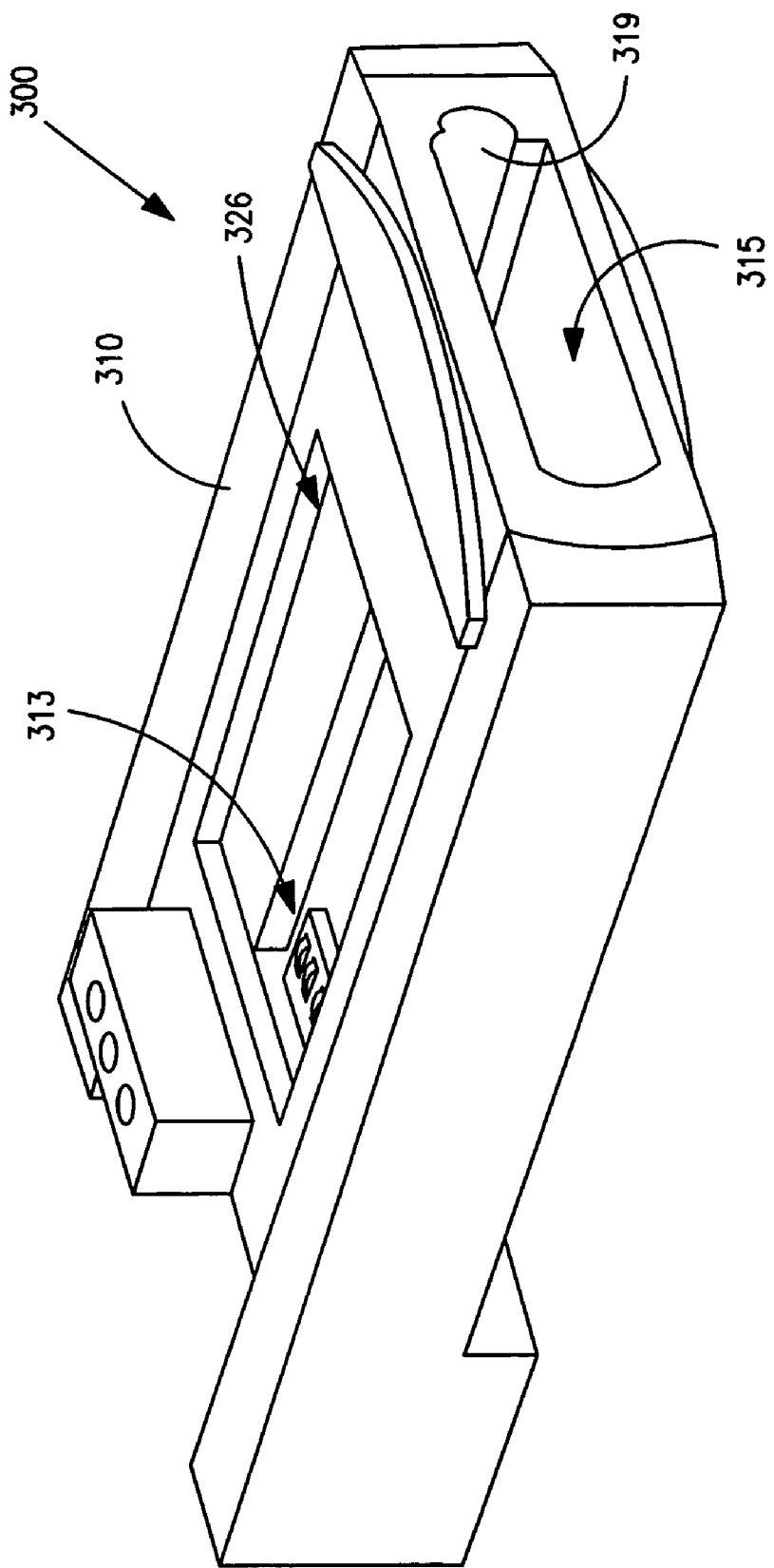
FIG. 6 is a perspective view of one embodiment of a cartridge in which the sample holder of FIG. 5 may be inserted.
Figure 7:
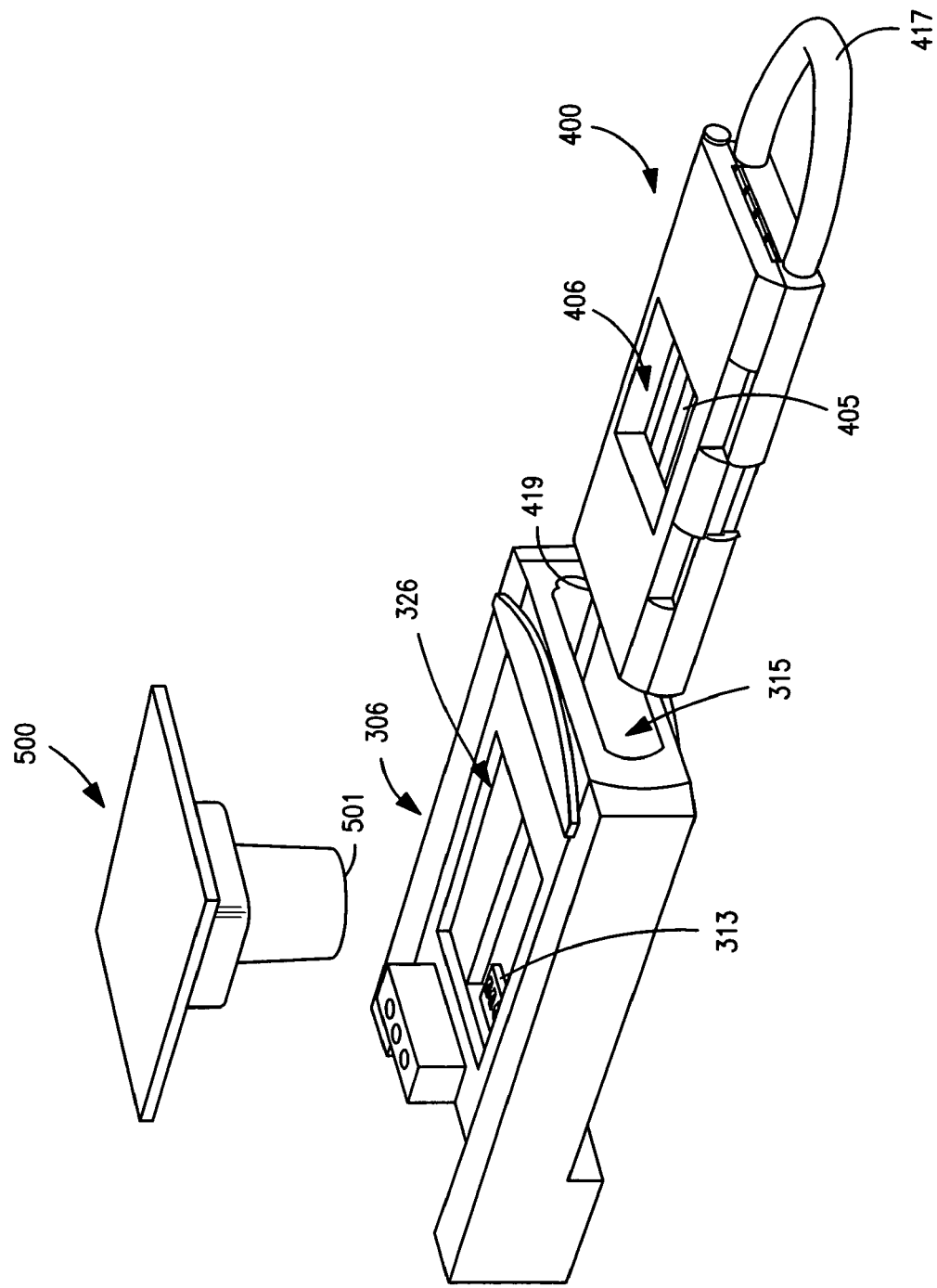
FIG. 7 is a perspective view of one embodiment of an optical detection system that utilizes the cartridge of FIG. 6 and the sample holder of FIG. 5.

As shown, one or more assay strips 405 may be disposed within an interior of the sample holder 400 defined between the lower portion 402 and upper portion 403. In this particular embodiment, the support card (not shown) of the assay strips 405 is also laminated to EL devices 412. This allows the EL devices 412 to be positioned close to the assay strips 405 during use to optimize the signal-to-noise ratio of the optical detection system. The EL devices 412 may be placed into electrical contact with leads in a variety of different ways. For example, the lower surface of the EL devices (e.g., cathode-side) may be placed adjacent to eight (8) holes 409, although any number of holes may of course be utilized. Referring to FIGS. 6 and 7, these holes 409 may be positioned adjacent to eight (8) corresponding leads 313 (only 3 of which are shown in FIGS. 6 and 7) of a cartridge 300. Specifically, a user may align one end 419 of the holder 400 with a sample port 315 defined by a body portion 310 of the cartridge 300, and thereafter slide the sample holder 400 through the sample port 315 via parallel tracks 319 until the holes 409 are positioned over the leads 313. In this manner, the lower side (e.g., cathode-side) of the EL devices 412 is placed into electrical contact with the leads 313. Although not specifically illustrated, an upper surface of the EL devices 412 (e.g., anode-side) may also extend beyond the assay strips 405 and placed into electrical contact with leads. For example, leads (not shown) may be disposed on the inner surface of the upper portion 403 of the sample holder 400 (FIG. 5) so that when the holder is closed, the leads contact the extended portion of the upper surface of the EL devices 412. Thus, during use, the EL devices 412 generate illumination that contacts detection probes located on the assay strips 405. The detection probes produce a detection signal that travels through an upper window 406 of the sample holder 400 and an upper window 326 of the cartridge 300 before reaching a lens 501 of a camera 500.

Figure 9:
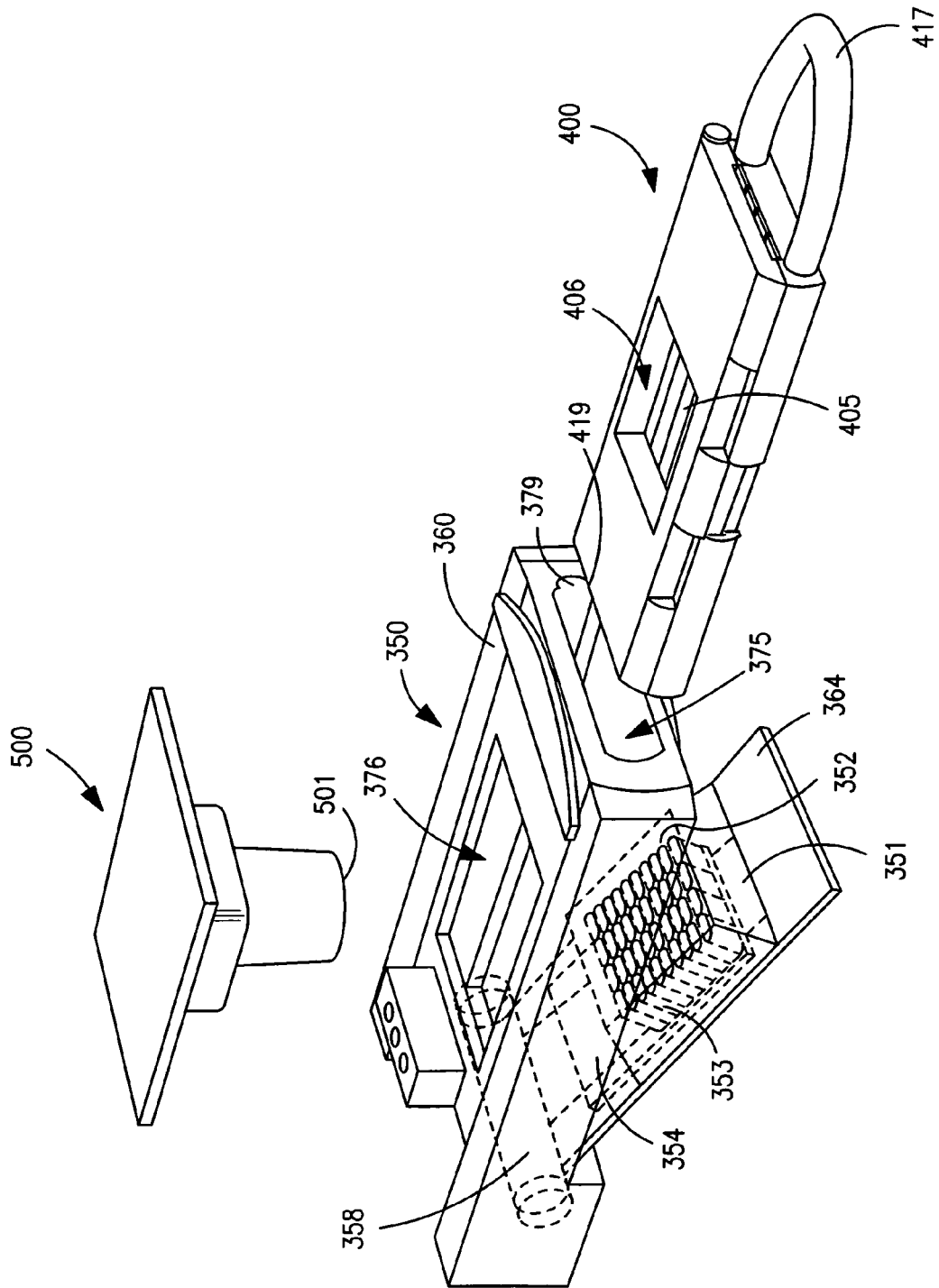
FIG. 9 is a perspective view of another embodiment of an optical detection system of the present invention that utilizes a sample holder and a cartridge in which an array of LEDs are disposed.
Figure 10:
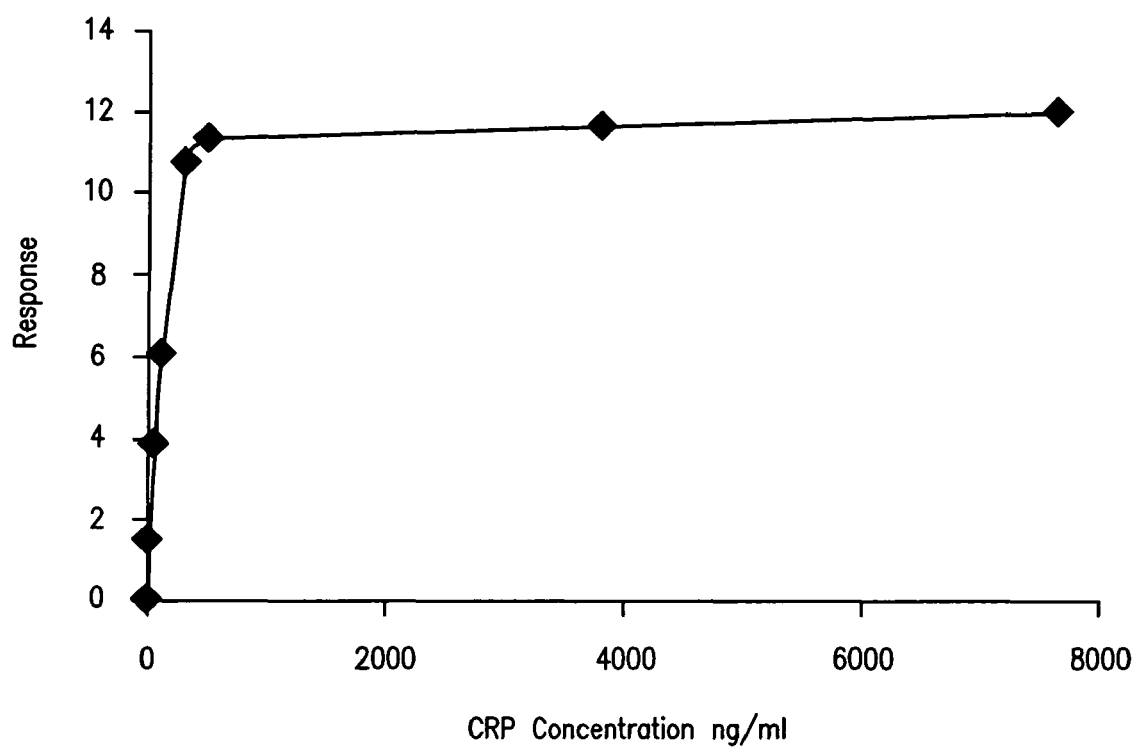
FIG. 10 graphically depicts the results of Example 1, in which the dose response is plotted versus CRP concentration (nanograms per milliliter).

Referring to FIG. 9, another embodiment of an optical detection is shown that employs a sample holder 400 and a cartridge 350. As shown, the cartridge 350 utilized in this embodiment has a body portion 360 that forms an upper window 376. The cartridge 350 also defines a sample insertion port 375 through which the sample holder 400 may be inserted via parallel tracks 379. For example, similar to the embodiment shown in FIG. 7, a user may grasp the sample holder 400 at the handle 417 and align an end 419 of the holder with the sample port 375 of the cartridge 350. Once aligned, the user may then slide the sample holder 400 through the sample port 375 until the upper window 406 of the sample holder 400 aligns with the upper window 376 of the cartridge 300.

In the embodiment shown in FIG. 9, a circuit board 354 containing an array of LEDs 353 is positioned under a base 351 to serve as the illumination source for the optical detection system. Although not specifically depicted, the lower surface of the sample holder 400 likewise contains an opening that accommodates the base 351 when the sample holder 400 is inserted into the cartridge 300. The base 351 is mounted to a door 364 that is connected to the body portion 360 via a hinge 358. When the door 364 is closed (manually or automatically), the LEDs 353 are placed in an active position. As illustrated, the base 351 and door 364 allow the LEDs 353 to be positioned very close to, and possibly even in contact with, assay strips 405 during use of the optical detection system. To ensure that the illumination produced by the LEDs 353 is able to reach the assay strips 405, the base 351 contains an upper surface 352 that is generally transmissive (e.g., optically diffuse, transparent, etc.) to the light emitted by the LEDs 353. For example, the upper surface 352 may have a relatively low thickness (e.g., 0.5 millimeters) and be formed from an optically diffuse polymeric material. Thus, upon transmitting through the upper surface 352, the illumination may contact detection probes located on the assay strips 405 to produce a detection signal, which travels through the upper window 406 of the sample holder 400 and the upper window 376 of the cartridge 300 before reaching a lens 501 of a camera 500. The remaining surfaces of the base 351 may or may not be transmissive to the light emitted by the LEDs 353.

Figure 8:
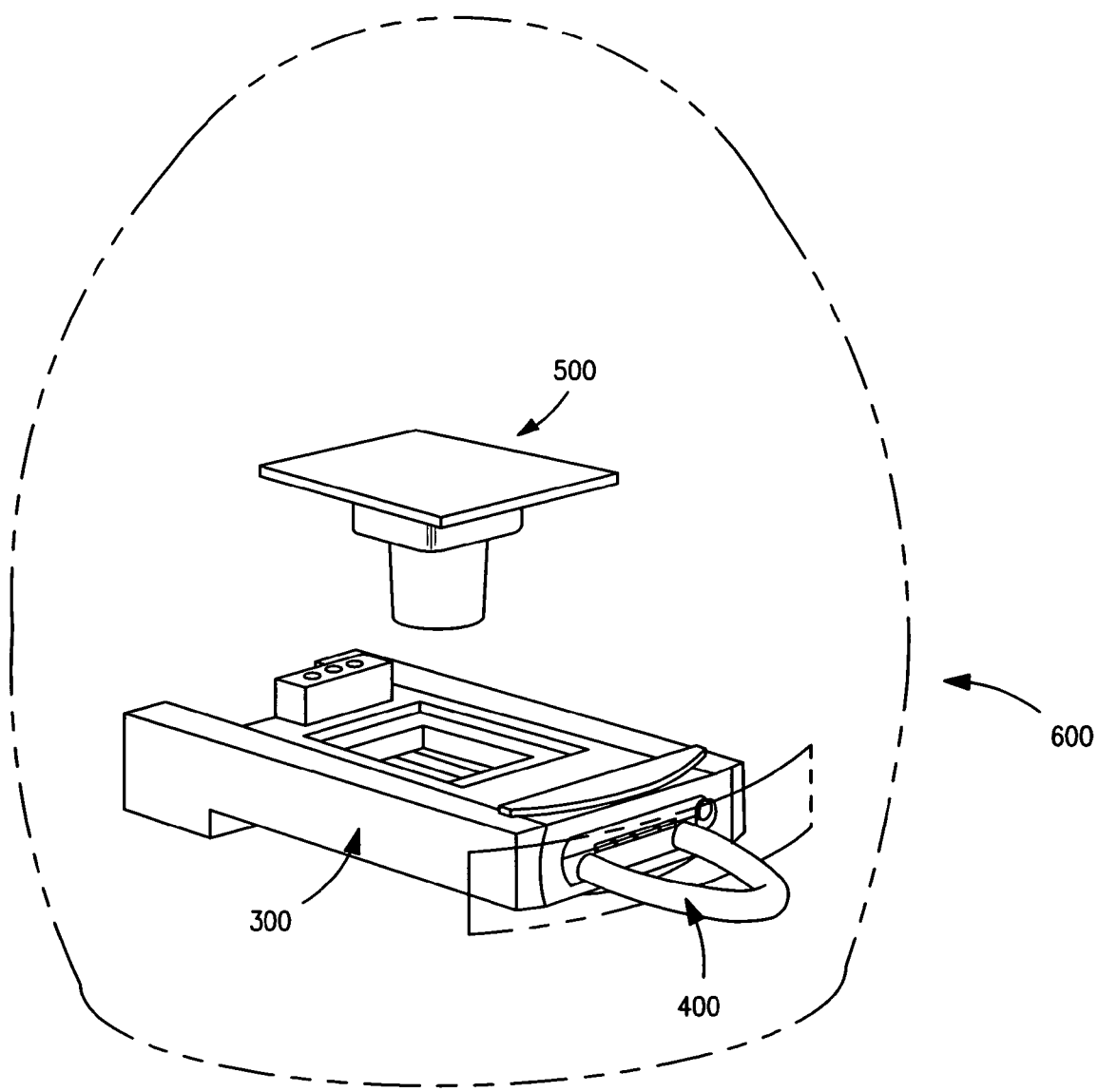
FIG. 8 is a perspective view of the optical detection system of FIG. 7 contained within an enclosure.

If desired, as shown in FIG. 8, the above-referenced components may be contained within an enclosure 600 that is not transmissive to the electromagnetic radiation emitted by the illumination source or registered by the detector to optically isolate the system. In the illustrated embodiment, for example, the sample holder 400 (FIG. 5), the cartridge 300 (FIG. 6), and the camera 500 (FIG. 7) are positioned within the enclosure 600. Although shown as having an oval shape, it should be understood that any other suitable shape and/or size may be employed, such as circular, square, rectangular, etc. Further, as would be readily recognized by those skilled in the art, other optical components may also be utilized and optionally contained within the enclosure 600, such as electronic circuitry, microprocessors, displays, mirrors, optical filters, lenses, and so forth.

Regardless of the specific manner in which the optical detection system is formed, qualitative, quantitative, or semi-quantitative determination of the presence or concentration of an analyte may be achieved in accordance with the present invention. For example, in one embodiment, the amount of the analyte may be quantitatively or semi-quantitatively determined by correlating the intensity of the signal, $I_s$, of the probes captured at the detection zone 31 with a predetermined analyte concentration. In some embodiments, the intensity of the signal, $I_s$, may also be compared with the intensity of the signal, $I_c$, of the probes captured at the calibration zone 32. The intensity of the signal, $I_s$, may be compared to the intensity of the signal, $I_c$. In this embodiment, the total amount of the probes at the calibration zone 32 is predetermined and known and thus may be used for calibration purposes. For example, in some embodiments (e.g., sandwich assays), the amount of analyte is directly proportional to the ratio of $I_s$ to $I_c$. In other embodiments (e.g., competitive assays), the amount of analyte is inversely proportional to the ratio of $I_s$ to $I_c$. Based upon the intensity range in which the detection zone 31 falls, the general concentration range for the analyte may be determined. As a result, calibration and sample testing may be conducted under approximately the same conditions at the same time, thus providing reliable quantitative or semi-quantitative results, with increased sensitivity.

If desired, the ratio of $I_s$ to $I_c$ may be plotted versus the analyte concentration for a range of known analyte concentrations to generate a calibration curve. To determine the quantity of analyte in an unknown test sample, the signal ratio may then be converted to analyte concentration according to the calibration curve. It should be noted that alternative mathematical relationships between $I_s$ and $I_c$ may be plotted versus the analyte concentration to generate the calibration curve. For example, in one embodiment, the value of $I_s/(I_s+I_c)$ may be plotted versus analyte concentration to generate the calibration curve.

A microprocessor may optionally be employed to convert the measurement from the detector 54 to a result that quantitatively or semi-quantitatively indicates the presence or concentration of the analyte. The microprocessor may include memory capability to allow the user to recall the last several results. Those skilled in the art will appreciate that any suitable computer-readable memory devices, such as RAM, ROM, EPROM, EEPROM, flash memory cards, digital video disks, Bernoulli cartridges, and so forth, may be used in the present invention. Optical density (grayscale) standards may also be used to facilitate a quantitative result as is well known in the art. Further, any known software may optionally be employed for data collection. For example, Logitech camera software may be used to collect data obtained from a Logitech camera-based detector. After the images are saved, they may be analyzed using any known commercial software package, such as ImageQuant from Molecular Dynamics of Sunnyvale, Calif. If desired, the results may be conveyed to a user using a liquid crystal (LCD) or LED display.

The present invention may be better understood with reference to the following examples.

EXAMPLE 1

The ability to form an optical detection system in accordance with the present invention was demonstrated. Initially, a nitrocellulose membrane (SHF-120, Millipore Corp. of Bedford, Mass.) was provided that was laminated to a Mylar® film support. The Mylar® film was attached directly to an electroluminescent (EL) device using a transparent adhesive obtained from Adhesives Research of Glen Rock, Pa. under the name "ARclear 8154." Care was taken to ensure the absence of bubbles, dust, and contaminants. The EL device was made by BKL, Inc. of Burr Ridge, Ill., and had a size of 60 millimeters×300 millimeters. In addition, the EL device also had a dual, broad emission maxima of 482 and 580 nanometers to give "white" light emission.

Goldline™ (a polylysine solution obtained from British Biocell International) was striped onto the membrane to form a calibration zone. Monoclonal antibody reactive toward C-reactive protein (BiosPacific, Inc., concentration of 1 milligram per milliliter) was immobilized on the porous membrane to form a detection zone. The card was then dried for 1 hour at a temperature of 37.5° C. After the card was removed from the oven, a cellulosic wicking pad (Millipore Co.) was attached to the end of the membrane closer to the calibration zone. The other end of the card, typically used to attach conjugation and sample pads, was removed. The card was then sliced into strips (4 mm×60 mm in size). Carboxylated blue latex beads (0.3 millimeters, Bang's Laboratories) were conjugated to monoclonal antibody reactive toward C-reactive protein (BiosPacific, Inc., concentration of 1 milligram per milliliter). The conjugate was mixed with various concentrations of C-reactive protein (CRP) serum standard (Kamiya), put into a micro-well plate, and tested against the half sticks. The blue detection and control lines developed within a minute.

After drying at ambient conditions for 1 hour, the lateral flow strips were loaded, four at a time, into a sample holder as shown in FIG. 5. The holder, when closed, immobilized the strips in such a manner that exposed electrodes on the underside of the EL device were aligned with holes in the holder. As shown in FIGS. 7 and 8, the sample holder was then inserted into an enclosure that housed a camera system. The purpose of the enclosure was to optically isolate the system from the external environment and ensure proper alignment between the camera and the assay devices. The camera was a Logitech QuickCam 3000 obtained from Logitech Inc. of Fremont, Calif., and used a USB connection to a standard desktop PC. The camera was fitted with a Finite Conjugate Micro Video Imaging Lens (8 mm focal length, NT54-853) from Edmund Industrial Optics of Barrington, N.J., and was positioned so that the surface of the nitrocellulose membrane was 47 millimeters from the imaging plane of the CCD. The EL device was powered by an AC power supply (ACM-500 from Behlman, Hauppauge, N.Y.) at 100 V and 400 Hz. Spring-loaded contacts (70AD/Male/4-up, Bourns, Riverside, Calif.) were mounted inside of the enclosure and made electrical contact through holes in the sample holder.

The images of the illuminated assay devices were collected and analyzed using Visual Basic (VB) software. The VB software used an ActiveX module (QCSDK1) to control the Logitech Twain device driver, which in turn controlled the CCD camera. A variety of image acquisition parameters were controlled, including Brightness, Exposure, Gain, Saturation and White Balance. The values of each were: Brightness =204 (out of 256), Exposure =1/300 sec, Gain =0 (out of 256), Saturation=120 (out of 256) and White Balance =120 (out of 256). Additionally, ten images were taken in succession and averaged to reduce noise. After the average image was acquired, regions of interest (ROI) for analysis (i.e., the bands and their surroundings) were identified by placing and sizing rectangles around the features and representative background areas. The average value of the pixels in the background region was calculated and used to normalize the pixels in the ROI. The data was also corrected with calibration data derived from images of blank strips. The average intensity of the pixels within the region of interest and the area of the pixels were calculated using the trapezium method. The results were displayed on the screen and charts were drawn with the intensity data. FIG. 9 illustrates the response curve obtained from various concentrations of C-reactive protein.

EXAMPLE 2

The ability to form an optical detection system in accordance with the present invention was demonstrated. Initially, a nitrocellulose membrane (SHF-120, Millipore Corp. of Bedford, Mass.) was provided that was laminated to a Mylar® film support. The Mylar® film was attached directly to an electroluminescent (EL) device using a transparent adhesive obtained from Adhesives Research of Glen Rock, Pa. under the name "ARclear 8154." Care was taken to ensure the absence of bubbles, dust, and contaminants. The EL device was made by BKL, Inc. of Burr Ridge, Ill., and had a size of 60 millimeters×300 millimeters. In addition, the EL device also had an emission maxima of 525 nanometers to give "green" light emission.

Monoclonal antibody reactive toward C-reactive protein (BiosPacific, Inc., concentration of 1 milligram per milliliter) was conjugated to colloidal gold particles having a size of 40 nanometers. The conjugate was then diluted in 2-millimolar hydrated sodium borate (Borax, pH 7.2) and 50% sucrose (final 10% sucrose). The conjugate was sprayed onto 5-millimeter wide glass fiber strips (Millipore GF33) at a rate of 5 microliters per centimeter and at a bed speed of 5 centimeters per second using a Kinematic 1600 dispenser. The sprayed conjugate strips were allowed to dry overnight at less than 20% relative humidity and at room temperature. The conjugate strips were then heat-sealed into impervious bags with desiccant. Goat-Anti-Mouse Antibody (GAM) was diluted in phosphate-buffered saline (PBS) to 0.1 milligram per milliliter and striped onto nitrocellulose membranes (HF120, Millipore) using the Kinematic 1600 dispenser at a dispense rate of 1 microliters per centimeter and at a bed speed of 5 centimeters per second. Biogenesis CRP (KC202004A, 2.59 milligrams per milliliter) was also striped neat below the GAM test line. The cards were left to dry at 37° C. for 1 hour. Upper wick and conjugate bands were attached with a 3-millimeter overlap and striped onto the nitrocellulose membrane. CRP standard (Scipac) was diluted in PBS to give the following final CRP concentrations: 100, 20, and 0 micrograms per milliliter. Two hundred microliters of each standard solution was applied to a strip. After drying at ambient conditions for 1 hour, several of the lateral flow strips were analyzed as described in Example 1. The results are set forth below in Table 1.

TABLE 1

Results of CRP Analysis

| Sample Concentration (µg/ml) | Peak Area | Peak Intensity |
|---|---|---|
| 100 | 0.52 | 0.60 |
| 20 | 1.80 | 0.66 |
| 0 | 6.02 | 0.99 |

EXAMPLE 3

The ability to form an optical detection system in accordance with the present invention was demonstrated. The EL device was made by BKL, Inc. of Burr Ridge, Ill., and had a size of 60 millimeters×300 millimeters. In addition, the EL device also had an emission maxima of 525 nanometers to give "green" light emission. The EL device was powered by an AC power supply (ACM-500 from Behiman, Hauppauge, N.Y.) at 100 V and 400 Hz. The EL device was cut into 4 mm×60 mm strips that were inserted into an enclosure as shown in FIGS. 5-8 using spring-loaded contacts (70AD/Male/4-up, Bourns, Riverside, Calif.) to make electrical contact through holes in the sample holder. The enclosure housed two blue-enhanced silicon photodiodes (PDB-V601, Photonic Detectors of Simi Valley, Calif.). The purpose of the enclosure was to optically isolate the system from the external environment and ensure proper alignment between the photodiodes and assay devices. The photodiodes were positioned so that they would be 100 micrometers from the surface of the membrane upon insertion. The leads from the two photodiodes were connected such that the diodes were wired in series, but reversed with respect to one another (i.e., the cathodes of the two photodiodes were soldered together). The two anode wires were connected to the probe leads of a multimeter (123 Industrial Scopemeter, Fluke, Everett, Wash.).

EXAMPLE 4

The ability to form an optical detection system in accordance with the present invention was demonstrated. Initially, lateral flow strips were provided that contained a nitrocellulose membrane (SHF-120, Millipore Corp. of Bedford, Mass.) laminated to a Mylar® film support. Goldline™ (a polylysine solution obtained from British Biocell International) was striped onto the membrane to form a calibration zone. Monoclonal antibody reactive toward C-reactive protein (BiosPacific, Inc., concentration of 1 milligram per milliliter) was immobilized on the porous membrane to form a detection zone. The sample was then dried for 1 hour at a temperature of 37.5° C. After the sample was removed from the oven, a cellulosic wicking pad (Millipore Co.) was attached to the end of the membrane closer to the calibration zone. The other end of the sample, typically used to attach conjugation and sample pads, was removed. The sample was then sliced into 4-millimeter strips. Carboxylated blue latex beads (0.3 millimeters, Bang's Laboratories) were conjugated to monoclonal antibody reactive toward C-reactive protein (BiosPacific, Inc., concentration of 1 milligram per milliliter). The conjugate was mixed with various concentrations of C-reactive protein (CRP) serum standard (Kamiya), put into a micro-well plate, and tested against the half sticks. The blue detection and control lines developed within a minute.

An array of LEDs was employed as the illumination source, such as shown in FIG. 9. Specifically, eleven 2×4 millimeter LEDs (SSL-LX2473GD, available from Lumex of Palatine, Ill.) were glued together to form an array that had a length of 22 millimeters and a width of 4 millimeters. The array size matched the size of the assay device. The light from the eleven LEDs was diffused using a 500-micrometer thick white polyamide sheet. The array of LEDs was wired in parallel and driven at between 2.4 and 3.5 VDC using a BK Precision 1735A DC Power Supply (Yorba Linda). Four such arrays (total of 44 LEDs were arranged next to each other in a cartridge (FIG. 9) with 0.5 mm spacing between the arrays.

As shown in FIG. 8, the cartridge was mounted inside of a light-tight enclosure along with a camera system. The purpose of the enclosure was to optically isolate the system from the external environment and ensure proper alignment between the camera and the assay devices. The camera was a Logitech QuickCam 3000 obtained from Logitech Inc. of Fremont, Calif., and used a USB connection to a standard desktop PC. The camera was fitted with a Finite Conjugate Micro Video Imaging Lens (8 mm focal length, NT54-853) from Edmund Industrial Optics of Barrington, N.J., and was positioned so that the surface of the nitrocellulose membrane was 47 millimeters from the imaging plane of the CCD. Four of the assay strips were also mounted into a sample holder (FIG. 5) with 0.5-millimeter spacing between the strips. When closed, the sample holder immobilized the strips to allow for intimate contact between the arrays of LEDs and the underside of the assay devices. Upon insertion in the enclosure, the LEDs rotated into place as shown in FIG. 9. The images of several illuminated assay devices were collected and analyzed as described in Example 1. The results are set forth below in Table 2.

TABLE 2

Results of CRP Analysis

| Sample Concentration (µg/ml) | Peak Area | Peak Intensity |
|---|---|---|
| 0.025 | 5.22 | 6.35 |
| 0.050 | 5.22 | 5.41 |
| 0.100 | 5.96 | 5.95 |
| 1.000 | 6.76 | 7.62 |

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An optical detection system for detecting the presence or quantity of an analyte residing in a test sample, said system comprising:
    an assay device that includes a porous membrane laminated directly to an optically diffuse film with an optically transparent adhesive located between the porous membrane and optically diffuse film, said porous membrane being in communication with detection probes, wherein said detection probes include non-fluorescent particles configured to produce a detection signal in the visible spectrum;
    a diffuse illumination source that provides electromagnetic radiation that causes said detection probes to produce said detection signal; and
    an electronic imaging detector that possesses spatial discrimination and registering said detection signal produced by said detection probes, wherein said illumination source and said detector are positioned on opposing sides of said assay device so that said porous membrane, said optically transparent adhesive, and said film are positioned in the electromagnetic radiation path defined between said illumination source and said detector, wherein the electromagnetic radiation is directly applied to either opposing side of said assay device; said porous membrane, said optically transparent adhesive, and said optically diffuse film being transmissive to said electromagnetic radiation and said detection signal, wherein said illumination source and said detector are positioned less than 5 millimeters from said assay device.

2. The optical detection system of claim 1, wherein a receptive material is immobilized within a detection zone defined by the porous membrane, said receptive material being configured to bind to at least a portion of said detection probes or complexes thereof.

3. The optical detection system of claim 1, wherein said assay device is contained within a sample holder.

4. The optical detection system of claim 3, wherein said illumination source is also positioned within said sample holder.

5. The optical detection system of claim 3, further comprising a cartridge that contains said illumination source, said cartridge defining a port that receives said sample holder.

6. The optical detection system of claim 1, wherein said illumination source is positioned adjacent to said porous membrane, and said detector is positioned adjacent to said film.

7. The optical detection system of claim 1, wherein said illumination source is positioned adjacent to said film, and said detector is positioned adjacent to said porous membrane.

8. The optical detection system of claim 1, wherein said illumination source, said detector, or both, are positioned less than about 3 millimeters from said assay device.

9. The optical detection system of claim 1, wherein said illumination source, said detector, or both, are positioned less than about 2 millimeters from said assay device.

10. The optical detection system of claim 1, wherein said illumination source is an electroluminescent device.

11. The optical detection system of claim 1, wherein said illumination source is an array of light-emitting diodes.

12. The optical detection system of claim 1, wherein said porous membrane is formed from nitrocellulose.

13. The optical detection system of claim 1, wherein said film is formed from a polymeric material.

14. The optical detection system of claim 1, wherein said film has a thickness of from about 100 to about 5,000 micrometers.

15. The optical detection system of claim 1, wherein said film has a thickness of from about 250 to about 1,000 micrometers.

16. The optical detection system of claim 1, wherein said detector includes a charge-coupled device (CCD), charge-injection device (CID), complementary-metal-oxide-semiconductor (CMOS) device, or a combination thereof.

17. The optical detection system of claim 1, wherein said detector includes a two-dimensional array of electronic fight sensors.

18. The optical detection system of claim 1, wherein the particles are latex particles labeled with a colored dye.

19. The optical detection system of claim 1, wherein the particles are metallic particles.

20. The optical detection system of claim 1, wherein an electroluminescent device acts as a support for the optical detection system.

* * * * *

UNITED STATES PATENT AND TRADEMARK OFFICE
CERTIFICATE OF CORRECTION

| | | |
|---|---|---|
| PATENT NO. | : 7,796,266 B2 | Page 1 of 1 |
| APPLICATION NO. | : 11/022287 | |
| DATED | : September 14, 2010 | |
| INVENTOR(S) | : David Samuel Cohen et al. | |

It is certified that error appears in the above-identified patent and that said Letters Patent is hereby corrected as shown below:

Col. 30, Claim 17, line 14 "fight" should read --light--.

Signed and Sealed this

Second Day of November, 2010

David J. Kappos
*Director of the United States Patent and Trademark Office*